United States Patent
Qin et al.

(10) Patent No.: US 11,991,920 B2
(45) Date of Patent: May 21, 2024

(54) ORGANIC-INORGANIC PEROVSKITE, FILM, LIGHT-EMITTING FILM, DELAYED FLUORESCENCE-EMITTING FILM, LIGHT-EMITTING ELEMENT, AND METHOD FOR PRODUCING LIGHT-EMITTING ELEMENT

(71) Applicant: KYULUX, INC., Fukuoka (JP)

(72) Inventors: Chuanjiang Qin, Fukuoka (JP); Toshinori Matsushima, Fukuoka (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 18/150,476

(22) Filed: Jan. 5, 2023

(65) Prior Publication Data
US 2023/0157149 A1 May 18, 2023

Related U.S. Application Data

(62) Division of application No. 16/761,667, filed as application No. PCT/JP2018/040758 on Nov. 1, 2018, now abandoned.

(30) Foreign Application Priority Data

Nov. 6, 2017 (JP) .................. 2017-213911

(51) Int. Cl.
C07F 7/24 (2006.01)
C09K 11/06 (2006.01)
(Continued)

(52) U.S. Cl.
CPC ............... H10K 85/30 (2023.02); C07F 7/24 (2013.01); C09K 11/06 (2013.01);
(Continued)

(58) Field of Classification Search
None
See application file for complete search history.

(56) References Cited

U.S. PATENT DOCUMENTS

2017/0152608 A1  6/2017  Jin et al.
2018/0083213 A1  3/2018  Snaith et al.

FOREIGN PATENT DOCUMENTS

CN  104662625 A  5/2015
JP  2014-78392 A  5/2014
(Continued)

OTHER PUBLICATIONS

Office Action dated Mar. 8, 2023 issued in the corresponding Chinese patent application No. 201880071621.5 with its English Machine Translation.
(Continued)

Primary Examiner — Sudhakar Katakam
Assistant Examiner — Jennifer C Sawyer
(74) Attorney, Agent, or Firm — BROWDY AND NEIMARK, PLLC

(57) ABSTRACT

An organic-inorganic perovskite satisfying $E_T < E_{T1}$ and $E_S - E_T \leq 0.1$ eV has a high emission efficiency. $E_S$ represents the excited singlet energy level in emission of an inorganic component, $E_T$ represents the excited triplet energy level in emission of an inorganic component, $E_{T1}$ represents the excited triplet energy level in emission of an organic component.

3 Claims, 7 Drawing Sheets

(51) Int. Cl.
  *H10K 85/30*    (2023.01)
  *H10K 50/11*    (2023.01)
  *H10K 102/00*   (2023.01)

(52) U.S. Cl.
  CPC .......... *C09K 2211/1007* (2013.01); *C09K 2211/1011* (2013.01); *H10K 50/11* (2023.02); *H10K 2102/351* (2023.02)

(56) References Cited

FOREIGN PATENT DOCUMENTS

| JP | 2017-193576 A | 10/2017 |
|---|---|---|
| WO | 2017/057313 A1 | 4/2017 |
| WO | 2017/086337 A1 | 5/2017 |

OTHER PUBLICATIONS

International Preliminary Report on Patentability, with English Translation, dated May 12, 2020, for corresponding International application No. PCT/JP2018/040758.

International Search Report dated Jan. 15, 2019, for corresponding PCT/JP2018/040758.

Matsushima, et al., N-channel field-effect transistors with an organic-inorganic layered perovskite semiconductor, Applied Physics Letters, 2016, pP. 253301-1-253301-5, vol. 109.

Quan, et al. Tailoring the Energy Landscape in Quasi-2D Halide Perovskites Enables Efficient Green-Light Emission, Nano Lett., 2017, pp. 3701-3709, vol. 17.

Qin, et al., Centrifugal-Coated Quasi-Two-Dimensional Perovskite $CsPb_2Br_5$ Films for Efficient and Stable Light-Emitting Diodes, J. Phys. Chem. Lett., 2017, pp. 5415-5421, 2017.

Yuan, et al., Perovskite energy funnels for efficient light-emitting diodes, Nature Nanotechnology, Oct. 2016, pp. 872-879, vol. 11.

European Search Report dated Oct. 23, 2020 from European patent application No. 18873546.8.

Quan, et al., Ligand-Stabilized Reduced-Dimensionality Perovskites, Journal of the American Chemical Society, 2016, pp. 2649-2655, vol. 138.

Chinese office action dated Aug. 29, 2022, in corresponding Chinese patent application No. 201880071621.5 and English translation.

Cohen, et al., High Efficiency and High Open Circuit Voltage in Quasi 2D Perovskite Based Solar Cells, Adv. Funct. Mater, 2017, pp. 1-7.

Fu, et al., Stabilization of the Metastable Lead Iodide Perovskite Phase via Surface Functionalization, Nano Lett., 17:4405-4414 (2017).

Gan, et al., 2D Homologous organic-inorganic hybrids as light-absorbers for planer and nanorod-based perovskite solar cells, Solar Energy Materials & Solar Cells, 162:93-102 (2017).

Smith, et al., A Layered Hybrid Perovskite Solar-Cell Absorber with Enhanced Moisture Stability, Angew. Chem., Int. Ed., 53:1-5 (2014).

[FIG. 2]
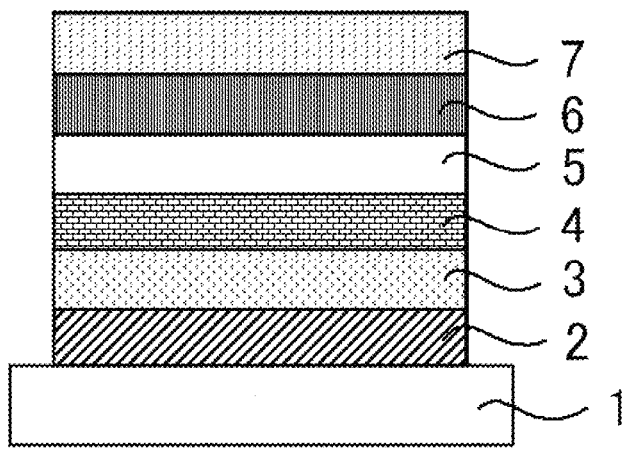
[FIG. 3]
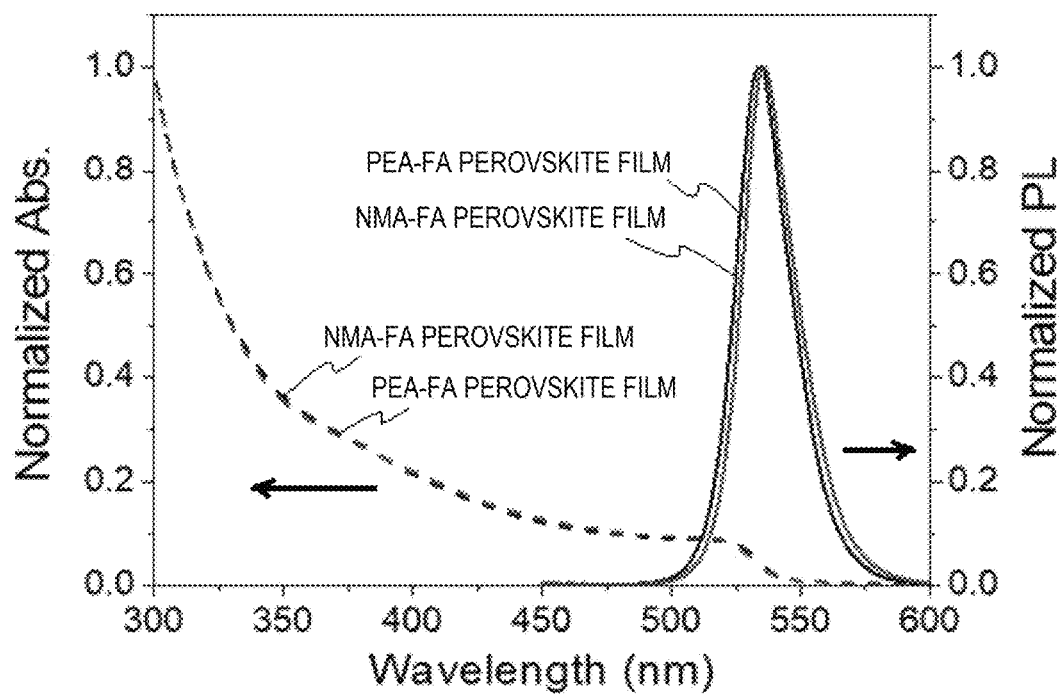

[FIG. 4]
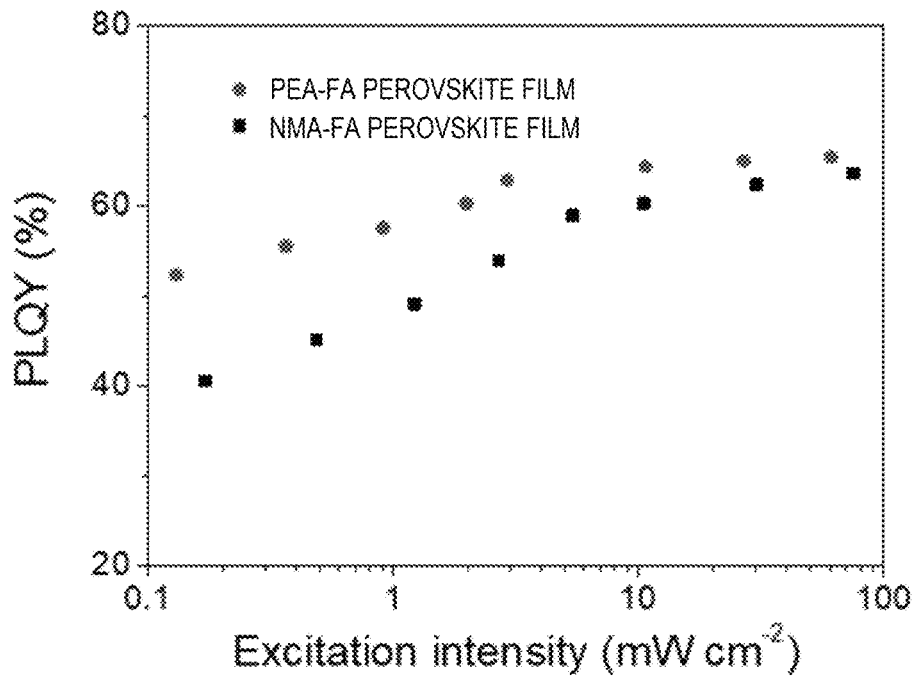
[FIG. 5]
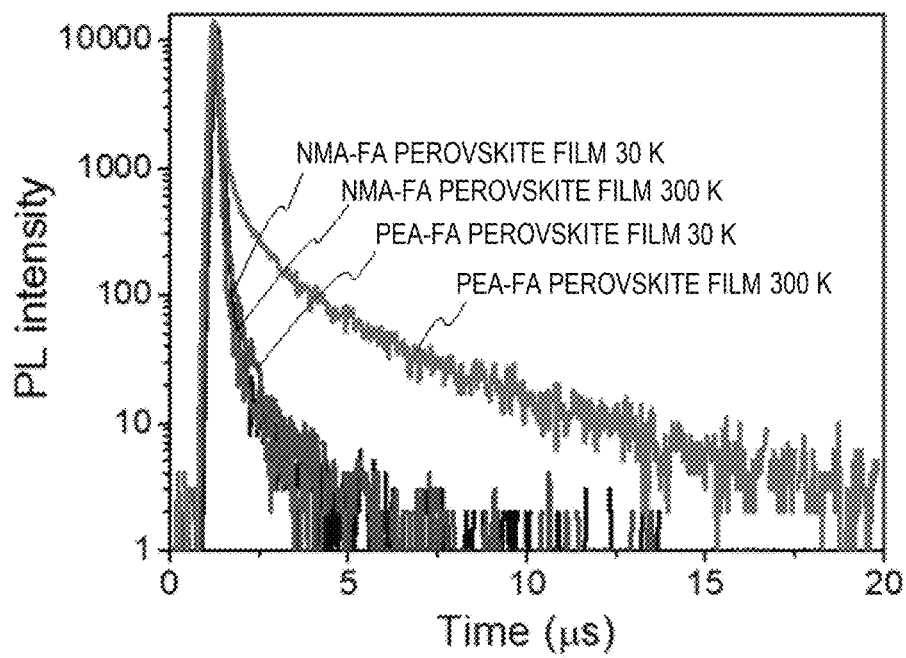

[FIG. 6]
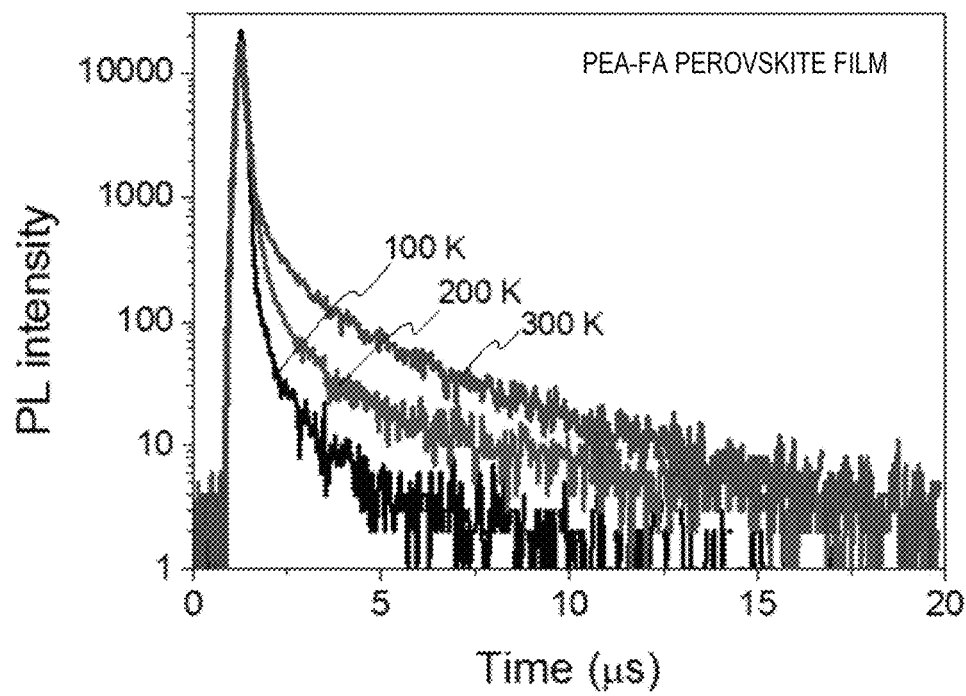
[FIG. 7]
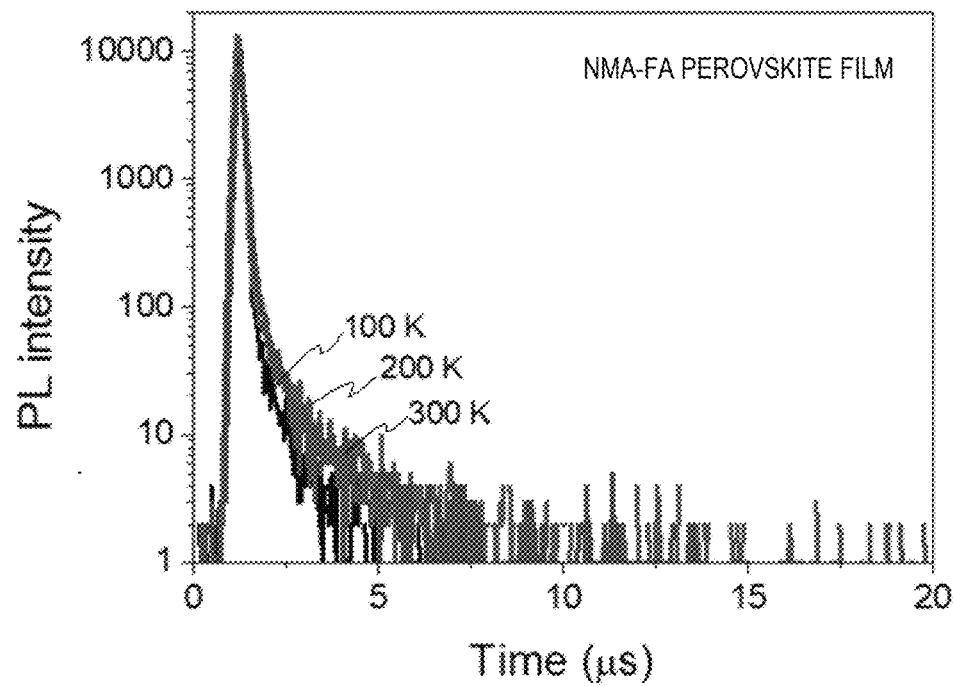

[FIG. 8]
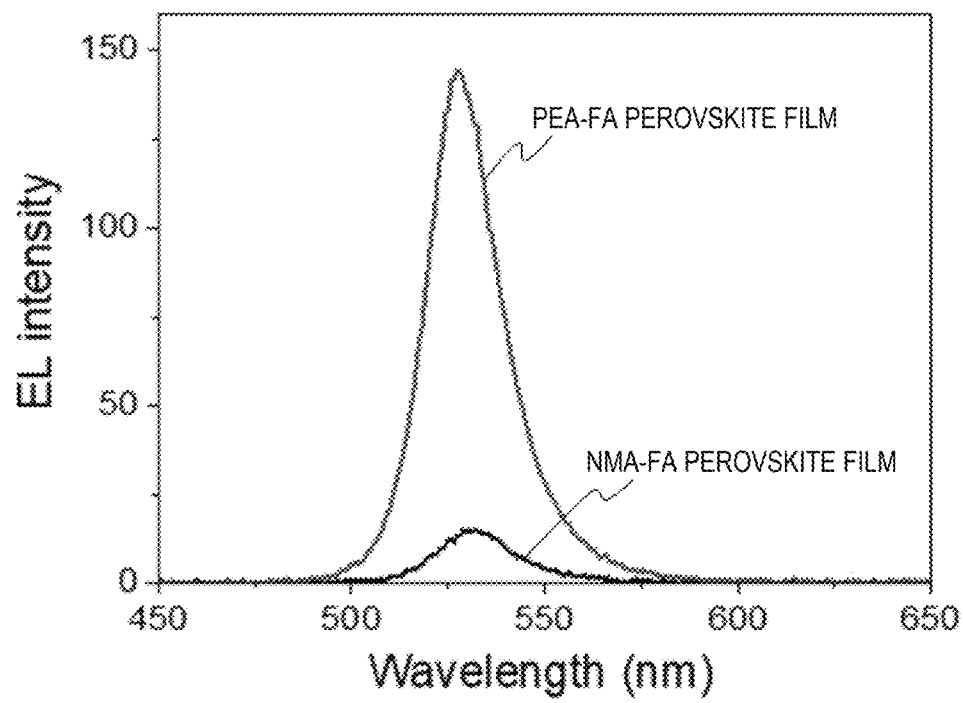
[FIG. 9]
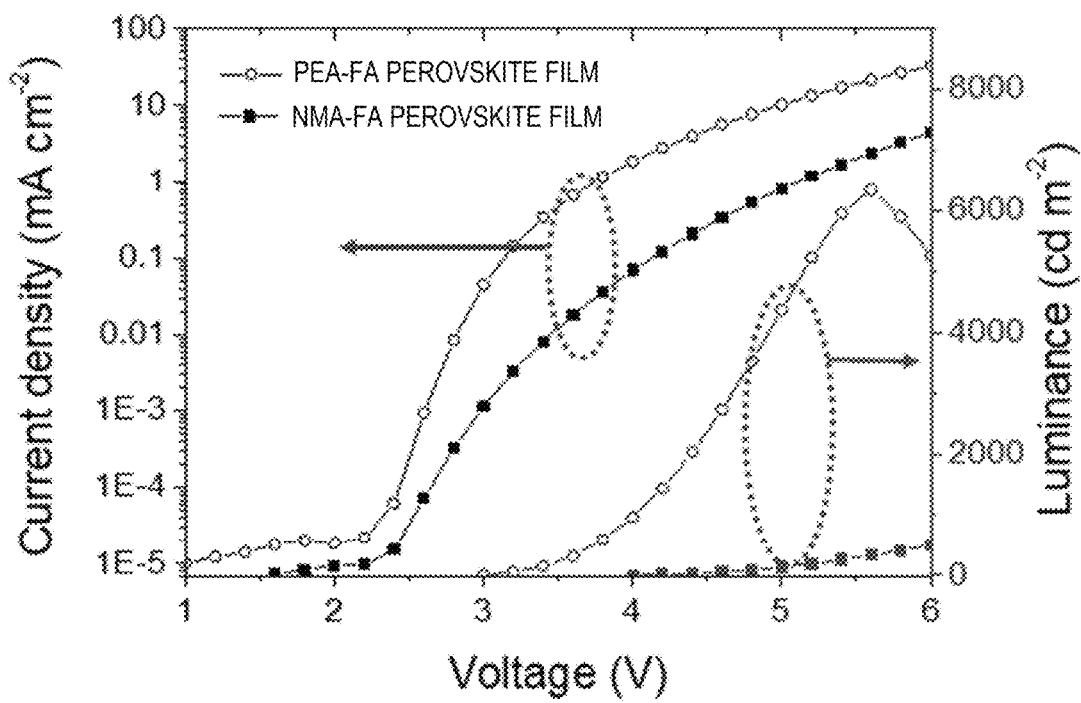

[FIG. 10]
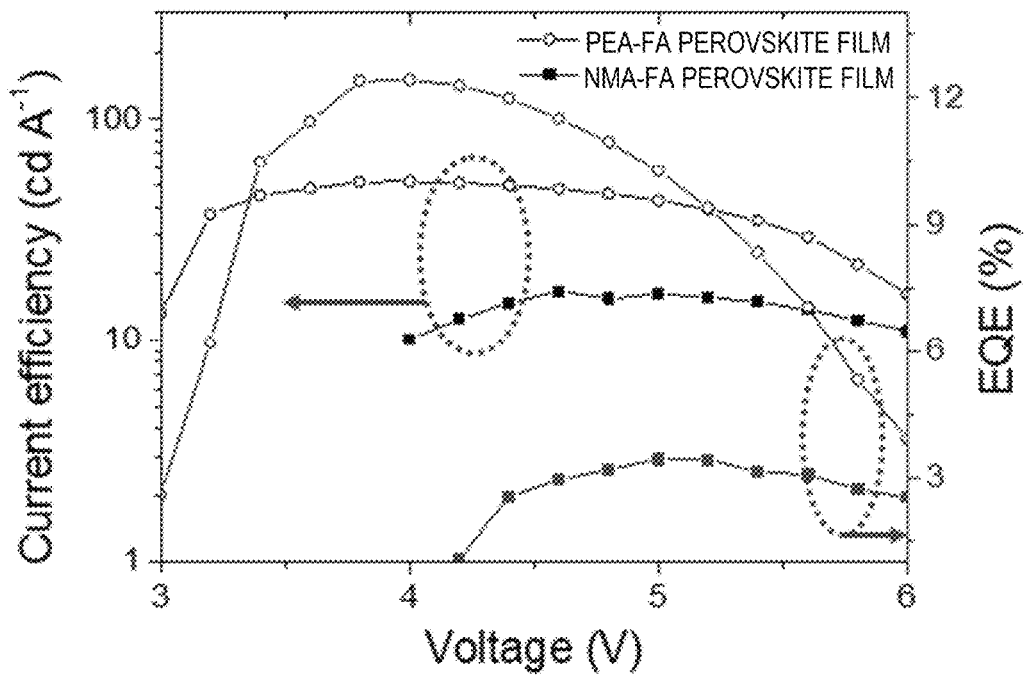
[FIG. 11]
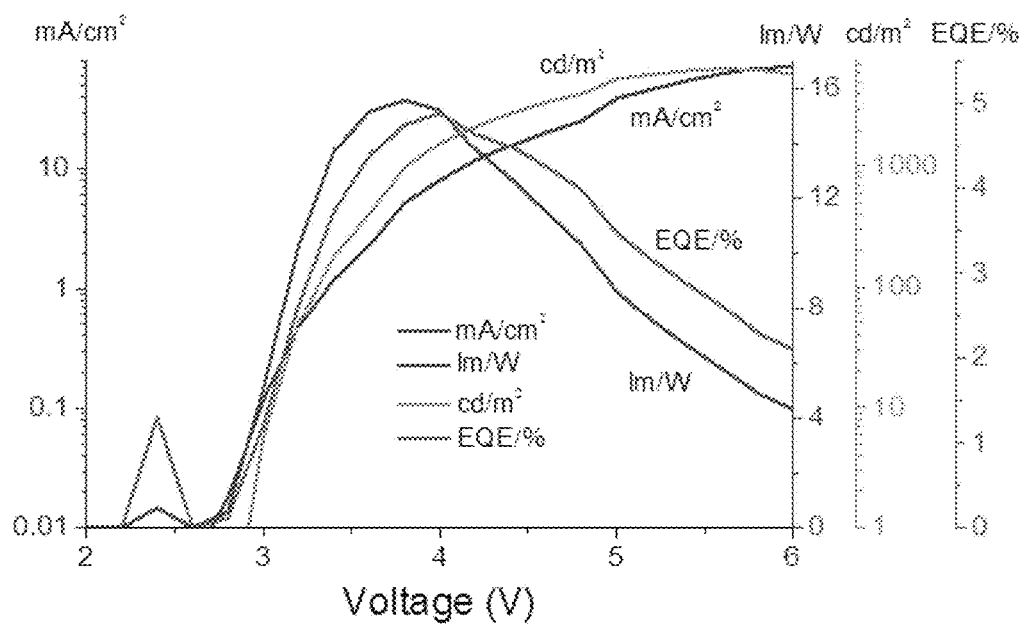

[FIG. 12]
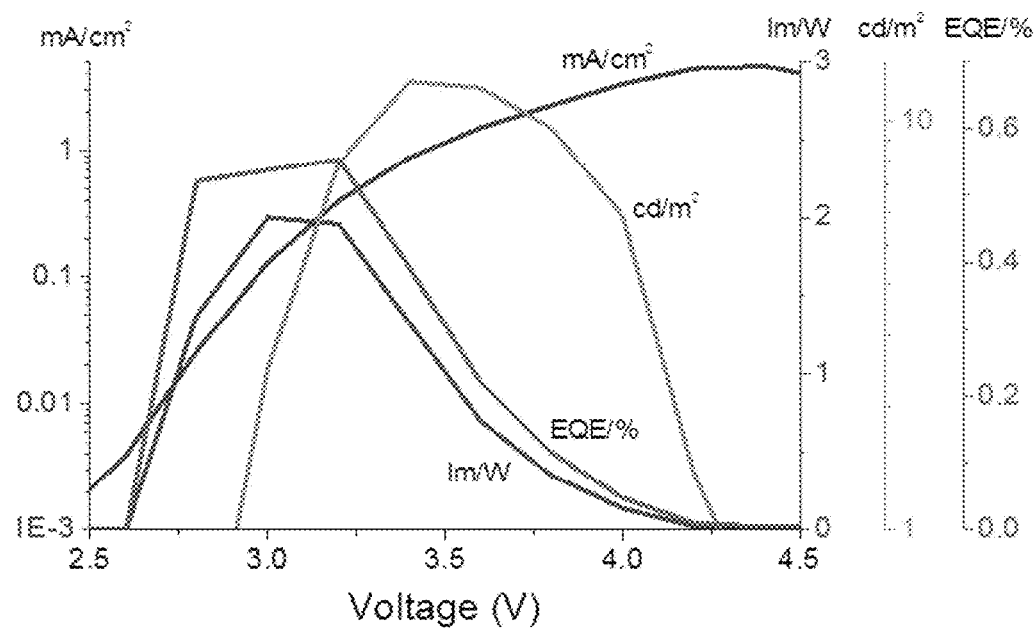

ORGANIC-INORGANIC PEROVSKITE, FILM, LIGHT-EMITTING FILM, DELAYED FLUORESCENCE-EMITTING FILM, LIGHT-EMITTING ELEMENT, AND METHOD FOR PRODUCING LIGHT-EMITTING ELEMENT

TECHNICAL FIELD

The present invention relates to an organic-inorganic perovskite useful as a material for light-emitting films for light-emitting devices.

BACKGROUND ART

An organic-inorganic perovskite is an ion compound composed of a monovalent cation such as an organic cation, a divalent metal ion such as $Sn^{2+}$ or $Pb^{2+}$, and a halide ion, in which these ions are regularly aligned so as to form a same crystal structure as that of a perovskite (perovskite structure). An organic-inorganic perovskite has semiconductor characteristics of inorganic substances along with flexibility and molecular planning diversity of organic substances, and is therefore expected as various functional materials, and development of devices using it is being actively promoted. Among them, there are found studies relating to light-emitting devices utilizing a film of an organic-inorganic perovskite as a light-emitting film.

For example, NPL 1 reports observation of near-IR emission in a light-emitting device using a film of $(C_6H_5C_2H_4NH_3)_2(CH_3NH_3)_{n-1}Pb_nI_{3n+1}$ (PEA-MA perovskite). NPL 2 reports observation of green emission in a light-emitting device using a film of PEA-MA perovskite. Here, a film of PEA-MA perovskite used in these literatures corresponds to a so-called quasi-2D (quasi-two-dimensional) perovskite which is composed of crystal lattices of a composition represented by $(CH_3NH_3)_{n-1}Pb_nI_{3n+1}$ and in which, on both sides of the inorganic layer having two or more layers of a two-dimensional array structure of a unit lattice, an organic layer is aligned with a cationic group of an organic cation represented by $C_6H_5C_2H_4NH_3$ facing the organic layer side. In these literatures, the number n of the layers having the two-dimensional array structure is varied to measure the emission efficiency of the devices, and among them, it is confirmed that a relatively high emission efficiency can be realized when n is 5.

CITATION LIST

Non-Patent Literature

Non-Patent Literature 1: Nature Nanotech. 2016, 11, 872
Non-Patent Literature 2: Nano Lett. 2017, DOI: 10.1021/acs.nanolett.7b00976

SUMMARY OF INVENTION

Technical Problem

As described above, NPLs 1 and 2 use a film of a PEA-MA perovskite in a light-emitting device, in which the number n of the inorganic layers having a two-dimensional array structure is controlled so as to attain a high emission efficiency. With that, the present inventors investigated the emission efficiency of the PEA-MA perovskite according to the same method, but have found that, even when only the number n of the inorganic layers is controlled in any manner, the emission efficiency peaks out at a certain level, and is not expected to be exponentially increased.

Given the situation, the present inventors have promoted studies of controlling the physical properties of an organic-inorganic perovskite from an innovative viewpoint different from conventional ones so as to improve the emission efficiency of the organic-inorganic perovskite.

Solution to Problem

As a result of further promoting assiduous investigations, the present inventors have reached findings that, when an organic-inorganic perovskite is so constituted that the excited singlet energy level ($E_S$) and excited triplet energy level ($E_T$) in emission of an inorganic component to constitute the organic-inorganic perovskite and the excited triplet energy level ($E_{T1}$) in emission of an organic component to constitute the organic-inorganic perovskite satisfy a predetermined relationship, then a dramatically high emission efficiency can be attained. The present invention is proposed here on the basis of these findings and specifically has the following constitution.

An organic-inorganic perovskite satisfying the following requirements (1) and (2):

$$E_T < E_{T1} \tag{1}$$

$$E_S - E_T \leq 0.1 \text{ eV} \tag{2}$$

wherein $E_S$ represents the excited singlet energy level in emission of an inorganic component constituting the organic-inorganic perovskite, $E_T$ represents the excited triplet energy level in emission of an inorganic component constituting the organic-inorganic perovskite, $E_{T1}$ represents the excited triplet energy level in emission of an organic component constituting the organic-inorganic perovskite.

The organic-inorganic perovskite according to [1], which emits delayed fluorescence.

The organic-inorganic perovskite according to [1] or [2], which is a quasi-2D perovskite.

The organic-inorganic perovskite according to any one of [1] to [3], which is represented by the following formula (10):

$$R_2A_{n-1}B_nX_{3n+1} \tag{10}$$

wherein R represents a monovalent organic cation, A represents a monovalent cation, B represents a divalent metal ion, X represents a halide ion, and n represents an integer of 2 or more,
and wherein the inorganic layer having a composition represented by $BX_{4n}$ in the formula (10) constitutes the inorganic component, and the organic cation represented by R in the formula (10) constitutes the organic component.

The organic-inorganic perovskite according to [4], wherein R in the formula (10) is an ammonium represented by the following formula (11):

$$Ar(CH_2)_{n1}NH_3^+ \tag{11}$$

wherein Ar represents an aromatic ring, and n1 represents an integer of 1 to 20.

The organic-inorganic perovskite according to [4] or [5], wherein A in the formula (10) is a formamidinium or a methylammonium.

The organic-inorganic perovskite according to any one of [4] to [6], wherein B in the formula (10) is $Pb^{2+}$.

The organic-inorganic perovskite according to any one of [4] to [7], wherein X in the formula (10) is Br—.

An organic-inorganic perovskite represented by the following formula (A) or the following formula (B):

$$PEA_2FA_{n-1}Pb_nBr_{3n+1} \quad (A)$$

$$PEA_2MA_{n-1}Pb_nBr_{3n+1} \quad (B)$$

wherein PEA represents a phenylethylammonium, FA represents a formamidinium, MA represents a methylammonium, and n represents an integer of 2 or more.

A film containing an organic-inorganic perovskite of any one of [1] to [9].

A light-emitting film containing an organic-inorganic perovskite of any one of [1] to [9].

A delayed fluorescence-emitting film containing an organic-inorganic perovskite of any one of [1] to [9].

A light-emitting device having a film of any one of [10] to [12].

The light-emitting device according to [13], which emits delayed fluorescence at 300 K.

A method for producing a light-emitting device wherein an organic-inorganic perovskite is so planned as to satisfy the following requirements, and a light-emitting device is produced using the organic-inorganic perovskite satisfying the following requirements (1) and (2):

$$E_T < E_{T1} \quad (1)$$

$$E_S - E_T \leq 0.1 \text{ eV} \quad (2)$$

wherein $E_S$ represents the excited singlet energy level in emission of an inorganic component constituting the organic-inorganic perovskite, $E_T$ represents the excited triplet energy level in emission of an inorganic component constituting the organic-inorganic perovskite, $E_{T1}$ represents the excited triplet energy level in emission of an organic component constituting the organic-inorganic perovskite.

Advantageous Effects of Invention

The organic-inorganic perovskite of the present invention is useful as a material for light-emitting films. A light-emitting device in which the light-emitting film is formed using the organic-inorganic perovskite of the present invention can realize a high emission efficiency.

BRIEF DESCRIPTION OF DRAWINGS

FIGS. 1A and 1B include schematic views for explaining an emission mechanism of the organic-inorganic perovskite of the present invention, in which FIG. 1A is a schematic view of showing an emission process of the organic-inorganic perovskite of the present invention, and FIG. 1B is a schematic view of showing an emission process of an organic-inorganic perovskite not satisfying the requirements defined in the present invention.

FIG. 2 is a schematic cross-sectional view showing a layer configuration example of an electroluminescent device of the present invention.

FIG. 3 shows photoabsorption spectra and emission spectra of a PEA-EA perovskite and an NMA-FA perovskite.

FIG. 4 is a graph showing excitation light intensity dependence of the photoluminescence quantum yield (PLQY) of a PEA-EA perovskite and an NMA-FA perovskite.

FIG. 5 shows transient decay curves of emission, measured at 30 K and 300 K, of a PEA-EA perovskite and an NMA-FA perovskite.

FIG. 6 shows transient decay curves of emission, measured at 100 K, 200 K and 300 K, of a PEA-EA perovskite.

FIG. 7 shows transient decay curves of emission, measured at 100 K, 200 K and 300 K, of an NMA-FA perovskite.

FIG. 8 shows emission spectra of an electroluminescent device using a PEA-EA perovskite and an electroluminescent device using an NMA-FA perovskite.

FIG. 9 shows graphs of current density-voltage-luminance characteristics of an electroluminescent device using a PEA-EA perovskite and an electroluminescent device using an NMA-FA perovskite.

FIG. 10 shows graphs of current density-voltage-external quantum efficiency (EQE) characteristics of an electroluminescent device using a PEA-EA perovskite and an electroluminescent device using an NMA-FA perovskite.

FIG. 11 shows graphs of current density-voltage-lamp efficiency, luminance, external quantum efficiency (EQE) characteristics of an electroluminescent device using a PEA-MA perovskite.

FIG. 12 shows graphs of current density-voltage-lamp efficiency, luminance, external quantum efficiency (EQE) characteristics of an electroluminescent device using a NMA-MA perovskite.

DESCRIPTION OF EMBODIMENTS

Hereinunder the contents of the present invention are described in detail. The constitutional elements may be described below with reference to representative embodiments and specific examples of the invention, but the invention is not limited to the embodiments and the examples. In the description herein, a numerical range expressed as "to" means a range that includes the numeral values before and after "to" as the lower limit and the upper limit. Also in this description, "main component" means a component having a largest content among the constituent components. The hydrogen atom that is present in the molecule of the compound used in the invention is not particularly limited in isotope species, and for example, all the hydrogen atoms in the molecule may be $^1H$, and all or a part of them may be $^2H$ (deuterium (D)).

<Organic-Inorganic Perovskite>

The organic-inorganic perovskite of the present invention satisfies the following requirements (1) and (2):

$$E_T < E_{T1} \quad (1)$$

$$E_S - E_T \leq 0.1 \text{ eV} \quad (2)$$

In the requirements (1) and (2), $E_S$ represents the excited singlet energy level in emission of an inorganic component constituting the organic-inorganic perovskite, $E_T$ represents the excited triplet energy level in emission of an inorganic component constituting the organic-inorganic perovskite, $E_{T1}$ represents the excited triplet energy level in emission of an organic component constituting the organic-inorganic perovskite.

In the present invention, the "excited singlet energy level in emission of an inorganic component constituting the organic-inorganic perovskite" means an energy level that causes an inorganic component to emit fluorescence via the energy level; and the "excited triplet energy level in emission of an inorganic component constituting the organic-inorganic perovskite" means an energy level that causes an inorganic component to emit phosphorescence via the energy level. Here, the "inorganic component" indicates an inorganic layer constituting the organic-inorganic perovskite, precisely an inorganic layer $BX_4$ of a two-dimensional configuration of unit lattices $BX_6$ where a divalent metal ion B is positioned at the center of an octahedron with sharing apexes of halide ions X.

In the present invention, the "excited triplet energy level in emission of an organic component constituting the organic-inorganic perovskite" means an energy level that causes an organic component to emit phosphorescence via the energy level. Here, the "organic component" indicates an organic cation of the organic-inorganic perovskite.

In this description, the "excited singlet energy level in emission of an organic component constituting the organic-inorganic perovskite" is represented by $E_{S1}$. Here, the "excited singlet energy level in emission of an organic component constituting the organic-inorganic perovskite" means an energy level that causes an organic component to emit fluorescence via the energy level.

Figure 1A:
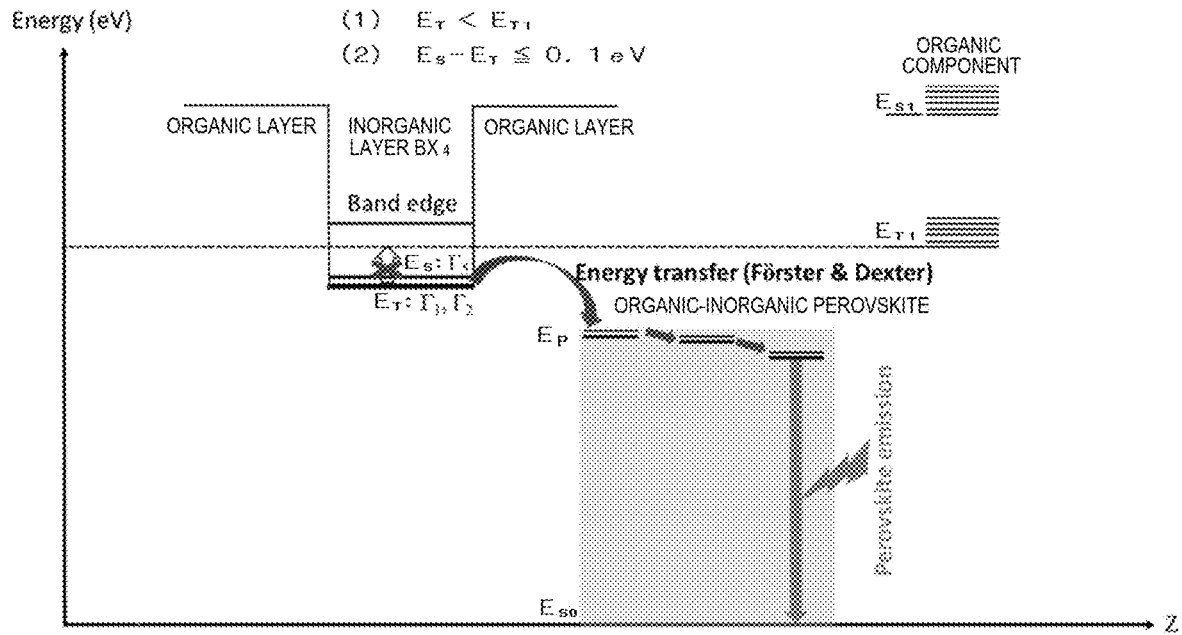
Figure 1B:
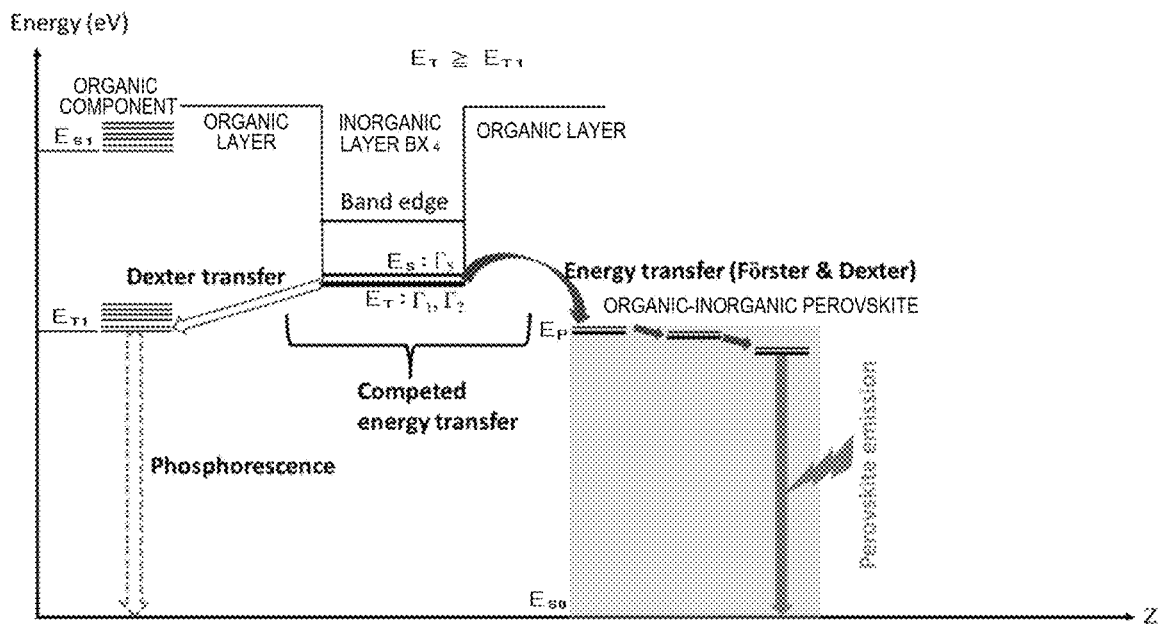

The organic-inorganic perovskite of the present invention satisfies the above-mentioned requirements (1) and (2) and therefore provides a high emission efficiency. This can be presumed to be because, in the organic-inorganic perovskite satisfying the above-mentioned requirements, the excited triplet energy formed in the inorganic component does not transfer to the organic component and can be efficiently utilized for emission from the organic-inorganic perovskite. Hereinunder the mechanism is described with reference to FIGS. 1A and 1B. FIGS. 1A and 1B show energy level diagrams of an organic-inorganic perovskite, an inorganic component and an organic component. $\Gamma_1$ and $\Gamma_2$ in the inorganic component each represent an excited triplet energy level $E_T$ in emission at a different vibration level, and $\Gamma_S$ represents an excited singlet energy level $E_S$ in emission. The number of vibration levels of the excited triplet energy level $E_T$ and the excited singlet energy level $E_S$ in emission of the inorganic component constituting the organic-inorganic perovskite of the present invention, the excited singlet energy level $E_{S1}$ and the excited triplet energy level $E_{T1}$ in emission of the organic component constituting the organic-inorganic perovskite are not limited to the number shown in FIGS. 1A and 1B. In the present invention, of each energy level $E_S$, $E_T$, and $E_{T1}$, at least the energy levels at a lowest vibration level satisfy the requirements (1) and (2).

First, when a singlet exciton and a triplet exciton form in the inorganic component constituting the organic-inorganic perovskite through excitation light irradiation or current injection, the energy of the singlet exciton transfers to the excited singlet energy level EP of the organic-inorganic perovskite according to a Dexter transfer mechanism or a Förster transfer mechanism, as shown in FIG. 1A, and via an energy transfer toward a lower excited singlet energy level, the energy transfers to a ground singlet energy level $S_0$ and deactivates with emitting fluorescence. Here, in the case where in the requirement (2) defined in the present invention, $E_S$-$E_T$≤0.1 eV is satisfied, the energy level difference between the excited single energy level $E_S$ in emission of the inorganic component and the excited triplet energy level $E_T$ in emission thereof is small, and therefore reverse intersystem crossing from the excited triplet state to the excited singlet state may readily occur, and the energy of the singlet exciton thereby formed may transfer to the excited single energy level $E_P$ of the organic-inorganic perovskite, and through energy transfer to a lower excited singlet energy level, the energy transfers to a ground singlet energy level $S_0$ and deactivates with emitting fluorescence. The fluorescence to be emitted at that time is observed as a delayed fluorescence having a longer emission lifetime than that of the fluorescence to be derived from the singlet exciton formed directly in the inorganic component through current injection. In that manner, in the system satisfying the requirement (2), from both the singlet exciton directly formed in the inorganic component through current injection and the singlet exciton formed via the reverse intersystem crossing from the excited triplet state to the excited singlet state, energy is supplied to the excited single energy level $E_P$ of the organic-inorganic perovskite, and therefore the system emits efficiently as compared with a system not satisfying the requirement (2).

However, as shown in FIG. 1B, in the case where the requirement (1) defined in the present invention $E_T$<$E_{T1}$ is not satisfied, that is, in the case where $E_T$≥$E_{T1}$, the excited triplet energy level $E_{T1}$ in emission of the organic component is smaller than the excited triplet energy level $E_T$ in emission of the inorganic component, and therefore the energy of the triplet exciton formed in the inorganic component transfers to the excited triplet energy level $E_{T1}$ in emission of the organic component, and conversion from the triplet exciton to the singlet exciton through reverse intersystem crossing does not occur sufficiently. Consequently, the energy of the triplet exciton formed in the inorganic component could not be efficiently utilized for fluorescence emission of the organic-inorganic perovskite.

As opposed to this, the organic-inorganic perovskite of the present invention satisfies the above-mentioned requirement (1) and additionally the requirement (2) $E_T$<$E_{T1}$, and therefore in this, the energy of the triplet exciton formed in the inorganic component does not transfer to the excited triplet energy level $E_{T1}$ in emission of the organic component, and conversion from the triplet exciton to the singlet exciton through reverse intersystem crossing occurs at a high probability. Consequently, both the singlet exciton and the triplet exciton formed in the inorganic component can be efficiently utilized for fluorescence emission and delayed fluorescence emission of the organic-inorganic perovskite, and the perovskite secures a high emission efficiency. For example, the probability of formation of a singlet exciton and a triplet exciton to form through current excitation is 25%/75%, and according to this mechanism, in principle, all the excitons can be singlet excitons and it is possible to attain an internal quantum yield of 100%.

Here, from the viewpoint of realizing a higher emission efficiency, $E_S$-$E_T$ in the requirement (2) is preferably 0.5 eV or less, more preferably 0.2 eV or less, and even more preferably 0.1 eV or less. In addition, in the requirement (1), the difference ($E_{T1}$-$E_T$) between the excited triplet energy level ($E_{T1}$) in emission of the organic component and the excited triplet energy level ($E_T$) in emission of the inorganic component is preferably 0.01 eV or more. The relationship between the excited singlet energy level ($E_{S1}$) in emission of the organic component and the excited singlet energy level ($E_S$) in emission of the inorganic component is preferably $E_S$<$E_{S1}$, and the difference therebetween ($E_{S1}$-$E_S$) is preferably 0.01 eV or more.

The excited singlet energy level ($E_S$) and the excited triplet energy level ($E_T$) in emission of the inorganic component constituting the organic-inorganic perovskite of the present invention, the energy difference therebetween ($E_S$-$E_T$), and the excited singlet energy level ($E_{S1}$) and the excited triplet energy level ($E_{T1}$) in emission of the organic component constituting the organic-inorganic perovskite are measured as follows. Here, the compound to be analyzed in measuring $E_S$ and $E_T$ thereof is the inorganic component constituting the organic-inorganic perovskite, and the compound to be analyzed in measuring $E_{S1}$ and $E_{T1}$ thereof is the organic cation constituting the organic-inorganic perovskite.

(1) Excited singlet energy level ($E_S$) in emission of organic component and excited singlet energy level ($E_{S1}$) in emission of organic component A solution of an organic-inorganic perovskite, that is, a compound to be analyzed is applied onto an Si substrate and dried to form thereon a sample of an organic-inorganic perovskite film having a thickness of 160 nm. At 30 K, the fluorescence spectrum with a 337 nm excitation light of the sample is measured. Here, emission immediately after excitation light incidence up to 100 nanoseconds after the light incidence is integrated to plot a fluorescence spectrum on a graph where the vertical axis indicates emission intensity and the horizontal axis indicates wavelength. A tangent line is drawn to the rising on the short wavelength side of the fluorescence spectrum, and a wavelength value λedge [nm] at the intersection between the tangent line and the horizontal axis is read. The wavelength value is converted into an energy value according to the following conversion expression to calculate the excited singlet energy level $E_S$ or $E_{S1}$ in emission.

Conversion Expression:Excited singlet energy level in emission[eV]=1239.85/λedge For the measurement of the fluorescence spectrum, for example, a nitrogen laser (Lasertechnik Berlin's MNL200) can be used as an excitation light source and a streak camera (Hamamatsu Photonics' C4334) can be used as a detector.

(2) Excited triplet energy level ($E_T$) in emission of inorganic component and excited triplet energy level ($E_{T1}$) in emission of inorganic component The same sample as that for measurement of the excited singlet energy level in emission is cooled to 30 K, and the sample is irradiated with a 337 nm excitation light, and using a streak camera, the phosphorescence intensity from the sample is measured. The emission from 1 millisecond after irradiation with the excitation light to 20 milliseconds after the irradiation is integrated to plot a phosphorescence spectrum on a graph where the vertical axis indicates emission intensity and the horizontal axis indicates wavelength. A tangent line is drawn to the rising on the short wavelength side of the phosphorescence spectrum, and a wavelength value λedge [nm] at the intersection between the tangent line and the horizontal axis is read. The wavelength value is converted into an energy value according to the following conversion expression to calculate the excited triplet energy level $E_T$ or $E_{T1}$ in emission.

Conversion Expression: Excited triplet energy level in emission [$eV$]=1239.85/λedge The tangent line to the rising of the phosphorescence spectrum on the short wavelength side is drawn as follows. While moving on the spectral curve from the short wavelength side of the phosphorescence spectrum toward the maximum value on the shortest wavelength side among the maximum values of the spectrum, a tangent line at each point on the curve toward the long wavelength side is taken into consideration. With rising thereof (that is, with increase in the vertical axis), the inclination of the tangent line increases. The tangent line drawn at the point at which the inclination value has a maximum value is referred to as the tangent line to the rising on the short wavelength side of the phosphorescence spectrum.

The maximum point having a peak intensity of 10% or less of the maximum peak intensity of the spectrum is not included in the maximum value on the above-mentioned shortest wavelength side, and the tangent line drawn at the point which is closest to the maximum value on the shortest wavelength side and at which the inclination value has a maximum value is referred to as the tangent line to the rising on the short wavelength side of the phosphorescence spectrum.

(3) Difference ($E_S$-$E_T$) between excited singlet energy level ($E_S$) and the excited triplet energy level ($E_T$) in emission of inorganic component ($E_S$-$E_T$) can be determined by subtracting the measured value of the excited triplet energy level ($E_T$) in emission according to the method (2) from the measured value of the excited singlet energy level ($E_S$) in emission according to the method (1).

The organic-inorganic perovskite of the present invention is an ion compound containing at least an organic cation, a divalent metal ion and a halide ion, and may additionally contain any other ion such as a monovalent cation. The other ion may be an organic ion or an inorganic ion. The organic-inorganic perovskite of the present invention contains an inorganic semiconductor layer and an organic component, and may be any of a two-dimensional perovskite, a quasi-two-dimensional perovskite or a three-dimensional perovskite, but a two-dimensional perovskite and a quasi-two-dimensional perovskite are preferred, and a quasi-two-dimensional perovskite is more preferred. Here, a two-dimensional perovskite has an inorganic semiconductor layer such that the inorganic skeleton corresponding to the octahedral part of a perovskite-type structure is formed in two-dimensional alignment, and an organic layer such that the cationic group of an organic cation is aligned facing the inorganic semiconductor layer side, and a quasi-two-dimensional perovskite has layers corresponding to the inorganic semiconductor layer and the organic layer of the two-dimensional perovskite in which, however, the inorganic semiconductor layer has two or more layers of a two-dimensional alignment structure and a monovalent cation is arranged at the position corresponding to each apex of the cubic crystal of the perovskite-type structure.

Preferred examples of the organic-inorganic perovskite are described below with reference to a quasi-two-dimensional perovskite.

[Quasi-Two-Dimensional Perovskite]

A quasi-two-dimensional perovskite of the organic-inorganic perovskite of the present invention is preferably a compound represented by the following formula (10).

(10)

In the formula (10), R represents a monovalent organic cation, A represents a monovalent cation, B represents a divalent metal ion, X represents a halide ion, and n represents an integer of 2 or more. Two R's, plural B's and plural X's each may be the same as or different from each other. Plural A's, if any, may be the same as or different from each other.

In the compound represented by the formula (10), a crystal lattice having the composition represented by $A_{n-1}B_nX_{3n+1}$ constitutes an inorganic semiconductor layer, and the monovalent organic cation represented by R constitutes an organic component. n corresponds to the number of layers having a two-dimensional alignment structure in the inorganic semiconductor layer, and is preferably an integer of 2 to 100.

The monovalent organic cation represented by R preferably has an aromatic ring, more preferably has an alkylene group and an aromatic ring, even more preferably has a structure of an alkylene group and an aromatic ring linking to each other, even more preferably is an ammonium having a structure of an alkylene group and an aromatic ring linking to each other, and is especially preferably an ammonium represented by the following formula (11).

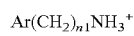
(11)

In the formula (11), Ar represents an aromatic ring, and n1 represents an integer of 1 to 20.

The aromatic ring that the organic cation has may be an aromatic hydrocarbon or an aromatic hetero ring, but is preferably an aromatic hydrocarbon. The hetero atom of the aromatic hetero ring includes a nitrogen atom, an oxygen atom and a sulfur atom. The aromatic hydrocarbon is preferably a benzene ring or a condensed polycyclic hydrocarbon having a structure of condensed plural benzene rings, and a benzene ring; a naphthalene ring, a phenanthrene ring, an anthracene ring, a chrysene ring, a tetracene ring, and a perylene ring are preferred, a benzene ring, and a naphthalene ring are more preferred, and a benzene ring is even more preferred. The aromatic hetero ring is preferably a pyridine ring, a pyrazine ring, a pyrimidine ring, a pyridazine ring, a pyrrole ring, a thiophene ring, a furan ring, a carbazole ring, or a triazine ring; and a pyridine ring, a pyrazine ring, a pyrimidine ring, and a pyridazine ring are more preferred, and a pyridine ring is even more preferred. The aromatic ring that the organic cation has may have a substituent such as, for example, an alkyl group, an aryl group or a halogen atom (preferably a fluorine atom). The hydrogen atom existing in the aromatic ring or in the substituent bonding to the aromatic ring may be a deuterium atom.

The monovalent cation represented by A may be an organic cation or an inorganic cation. The monovalent cation includes a formamidinium, an ammonium and a cesium, and is preferably a formamidinium.

The divalent metal ion represented by B includes $Cu^{2+}$, $Ni^{2+}$, $Mn^{2+}$, $Fe^{2+}$, $co^{2+}$, $Pd^{2+}$, $Ge^{2+}$, $Sn^{2+}$, $Pb^{2+}$, and $Eu^{2+}$; and $Sn^{2+}$, and $Pb^{2+}$ are preferred, and $Pb^{2+}$ is more preferred.

The halide ion represented by X includes ions of fluorine, chlorine, bromine and iodine. The halide ions represented by plural X's may be all the same, or may be a combination of 2 or 3 kinds of halide ions. Preferably, plural X's are the same halide ions, and more preferably plural X's are all bromide ions.

Preferred examples of the compound represented by the formula (10) include compounds represented by the following formula (A) and compounds represented by the following formula (B). However, the organic-inorganic perovskite of the present invention is not limitatively interpreted by these examples.

$PEA_2FA_{n-1}Pb_nBr_{3n+1}$       (A)

$PEA_2MA_{n-1}Pb_nBr_{3n+1}$       (B)

In the formulae (A) and (B), PEA represents a phenylethylammonium, FA represents a formamidinium, MA represents a methylammonium, and n is an integer of 2 or more.

The compounds represented by the formulae (A) and (B) are novel compounds. For a method for synthesizing the compounds, reference may be made to the description in the section of [Film Formation Method] and (Example 1) to be given hereinunder.

<Film>

Next, the film of the present invention is described.

The film of the present invention contains the organic-inorganic perovskite of the present invention. For the description, the preferred range and the specific examples of the organic-inorganic perovskite, reference may be made to the corresponding description in the section of <Organic-Inorganic Perovskite>. As described above, the organic-inorganic perovskite of the present invention satisfies the requirements (1) and (2) and therefore can secure a high emission efficiency. Consequently, the film of the present invention can be effectively used as a light-emitting film. In particular, as satisfying the requirement (2), $E_S-E_T \leq 0.1$ eV, the organic-inorganic perovskite of the present invention can readily undergo reverse intersystem crossing from an excited triplet state to an excited singlet state in the organic component therein. Consequently, the organic-inorganic perovskite can emit light through both radiation deactivation from the excited singlet state derived from the singlet exciton directly formed in the inorganic component by excitation light irradiation or current injection, and radiation deactivation from the excited singlet state derived from the singlet exciton formed via reverse intersystem crossing. At that time, the radiation deactivation from the excited singlet state derived from the singlet exciton formed via reverse intersystem crossing is later than the radiation deactivation from the excited singlet state derived from the singlet exciton directly formed by current injection, and therefore the resultant light emission is observed as delayed fluorescence emission having a long emission lifetime. Accordingly, the film of the present invention can also be effectively used as a delayed fluorescence emitting film. The delayed fluorescence emitting film can be confirmed by the transient decay curve of emission at 300 K, in which both a fluorescent component having a short emission lifetime and a fluorescent component having a long emission lifetime (delayed fluorescent component) are seen.

[Film Formation Method]

The method for forming the film of the present invention is not specifically limited, and may be a dry process such as a vacuum evaporation method, or a wet process such as a solution coating method. Here, a solution coating method is advantageous in that film formation can be attained using a simple apparatus and for a short period of time, and production cost can be reduced and mass-production is easy. A vacuum evaporation method is advantageous in that a film having a better surface condition can be formed.

For example, for forming a film containing an organic-inorganic perovskite represented by $PEA_2FA_{n-1}Pb_nBr_{3n+1}$ according to a vacuum evaporation method, employable is a co-evaporation method of co-evaporating lead bromide (PbBr2), phenylethylammonium bromide (PEABr) and formamidinium bromide (FABr) from different evaporation sources. Films containing any other type of organic-inorganic perovskite can also be formed according to the method by co-evaporating a metal halide compound, a compound of a monovalent organic cation and a halide ion and a compound of any other monovalent cation and a halide ion.

For forming a film containing an organic-inorganic perovskite represented by $PEA_2FA_{n-1}Pb_nBr_{3n+1}$ according to a solution coating method, lead bromide (PbBr2), phenylethylammonium bromide (PEABr) and formamidinium bromide (FABr) are reacted in a solvent to prepare an organic-inorganic perovskite or a precursor thereof, and a coating liquid containing the organic-inorganic perovskite is applied onto the surface of support and dried to form a film thereon. Films containing any other perovskite compound represented by the formula and an organic light-emitting material can also be formed according to the method by synthesizing an organic-inorganic perovskite in a solvent, then applying a coating liquid that contains the organic-inorganic perovskite and an organic light-emitting material onto the surface of a support and drying the liquid thereon. If desired, coating with the coating liquid may be followed by baking treatment.

The coating method with a coating liquid is not specifically limited, and any conventionally-known coating method is employable, such as a gravure coating method, a bar coating method, a printing method, a spraying method, a spin coating method, a dipping method, or a die coating method. A spin coating method is preferred since a relatively thin coating film can be formed uniformly.

Not specifically limited, the solvent for the coating liquid may be any one capable of dissolving a perovskite compound. Specifically, examples thereof include esters (e.g., methyl formate, ethyl formate, propyl formate, pentyl formate, methyl acetate, ethyl acetate, pentyl acetate), ketones (e.g., γ-butyrolactone, N-methyl-2-pyrrolidone, acetone, dimethyl ketone, diisobutyl ketone, cyclopentanone, cyclohexanone, methylcyclohexanone), ethers (e.g., diethyl ether, methyl-tert-butyl ether, diisopropyl ether, dimethoxymethane, dimethoxyethane, 1,4-dioxane, 1,3-dioxolan, 4-methyldioxolan, tetrahydrofuran, methyltetrahydrofuran, anisole, phenetole), alcohols (e.g., methanol, ethanol, 1-propanol, 2-propanol, 1-butanol, 2-butanol, tert-butanol, 1-pentanol, 2-methyl-2-butanol, methoxypropanol, diacetone alcohol, cyclohexanol, 2-fluoroethanol, 2,2,2-trifluoroethanol, 2,2,3, 3-tetrafluoro-1-propanol), glycol ether (cellosolves) (e.g., ethylene glycol monomethyl ether, ethylene glycol monoethyl ether, ethylene glycol monobutyl ether, ethylene glycol monoethyl ether acetate, triethylene glycol dimethyl ether), amide solvents (e.g., N,N-dimethylformamide, acetamide, N,N-dimethylacetamide), nitrile solvents (e.g., acetonitrile, isobutyronitrile, propionitrile, methoxyacetonitrile), carbonate solvents (e.g., ethylene carbonate, propylene carbonate), halogenohydrocarbons (e.g., methylene chloride, dichloromethane, chloroform), hydrocarbons (e.g., n-pentane, cyclohexane, n-hexane, benzene, toluene, xylene), and dimethyl sulfoxide. In addition, also usable herein are those having any two or more functional groups of esters, ketones, ethers and alcohols (i.e., —O—, —CO—, —COO—, —OH), as well as those derived from esters, ketones, ethers and alcohols by substituting the hydrogen atom in the hydrocarbon moiety therein with a halogen atom (especially a fluorine atom).

The content of the perovskite compound in the coating liquid is preferably 1 to 50% by mass relative to the total amount of the coating liquid, more preferably 2 to 30% by mass, even more preferably 5 to 20% by mass. The content of the organic light-emitting material in the coating liquid is preferably 0.001% by mass or more and less than 50% by mass relative to the total amount of the perovskite compound and the organic light-emitting material.

Preferably, the coating liquid applied onto the surface of a support is dried spontaneously or by heating in an atmosphere purged with an inert gas such as nitrogen.

<Light-Emitting Device>

Next, the light-emitting device of the present invention is described.

The light-emitting device of the present invention has a film containing the organic-inorganic perovskite of the present invention. For the description, the preferred range and the specific examples of the film containing the organic-inorganic perovskite of the present invention, reference may be made to the description in the section of <Film>. The film of the present invention that the light-emitting device has may have any function and, for example, may be a light-emitting layer, or a delayed fluorescence-emitting layer, or may be used as both a light-emitting layer and a delayed fluorescence-emitting layer. The light-emitting device may have only one layer of a film containing the organic-inorganic perovskite of the present invention, or may have two or more layers of the film. In the case where the light-emitting device has two or more layers of a film containing the organic-inorganic perovskite of the present invention, the organic-inorganic perovskite that the films contain may be the same or different.

As described above, the organic-inorganic perovskite that the film of the present invention contains has a high emission efficiency, and therefore the light-emitting device containing the film can realize a high emission efficiency. In particular, the light-emitting device that emits delayed fluorescence at 300 K can secure an extremely high emission efficiency at room temperature. In addition, the organic-inorganic perovskite is inexpensive, and therefore using the film containing the perovskite, the material cost for the light-emitting device can be reduced.

[Layer Configuration of Light-Emitting Device]

The light-emitting device to which the present invention is applied may be a photoluminescent device (also expressed as a PL device) or may also be an electroluminescent device (also expressed as an EL device, and in the present invention, it is a perovskite electroluminescent device). The photoluminescent device has a structure having at least a light-emitting layer formed on a substrate. The electroluminescent device includes at least an anode, a cathode, and a light-emitting layer between the anode and the cathode. The film containing the organic-inorganic perovskite of the present invention can be favorably used as the light-emitting layer in these light-emitting devices. The film containing the organic-inorganic perovskite of the present invention attains an effect that realizes a high emission efficiency especially when applied to an electroluminescent device among such light-emitting devices.

The electroluminescent device includes a light-emitting layer that contains at least the organic-inorganic perovskite, and may be formed of such a light-emitting layer alone, or may include any other one or more organic layers in addition to the light-emitting layer. Such other organic layers may be selected, if desired, from among organic layers that constitute an organic electroluminescent device, including, for example, a hole transport layer, a hole injection layer, an electron blocking layer, a hole blocking layer, an electron injection layer, an electron transport layer, and an exciton blocking layer. The hole transport layer may be a hole injection transport layer that has a hole injection function, and the electron transport layer may be an electron injection transport layer that has an electron injection function. A configuration example of an electroluminescent device is shown in FIG. 2. In FIG. 2, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the electroluminescent device are described. The description of the substrate and the light-emitting layer given below may apply to the substrate and the light-emitting layer of a photoluminescent device.

(Substrate)

The electroluminescent device of the invention is preferably supported by a substrate. The substrate is not particularly limited and may be those that have been commonly used in an organic electroluminescent device, and examples thereof used include those formed of glass, transparent plastics, quartz and silicon.

(Anode)

The anode of the electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness of the anode may be generally selected from a range of from 10 to 1,000 nm, and preferably from 10 to 200 nm, while depending on the material used.

(Cathode)

The cathode is preferably formed of as an electrode material a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

(Light-Emitting Layer)

The light-emitting layer is a layer in which holes and electrons injected from an anode and a cathode are recombined to give excitons for light emission, and the layer is formed of a film (light-emitting film) containing the organic-inorganic perovskite of the present invention.

The light-emitting film for use for the light-emitting layer of the electroluminescent device preferably has a thickness of 20 to 500 nm, more preferably 50 to 300 nm.

(Injection Layer)

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

(Blocking Layer)

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

(Hole Blocking Layer)

The hole blocking layer has the function of an electron transport layer in a broad sense. The hole blocking layer has a function of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

(Electron Blocking Layer)

The electron blocking layer has the function of transporting holes in a broad sense. The electron blocking layer has a function of inhibiting electrons from reaching the hole transport layer while transporting holes, and thereby enhances the recombination probability of electrons and holes in the light-emitting layer.

(Exciton Blocking Layer)

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be inserted adjacent to the light-emitting layer on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy of the light-emitting layer, respectively, of the light-emitting material.

(Hole Transport Layer)

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

(Electron Transport Layer)

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

The electroluminescent device may use the film containing the organic-inorganic perovskite of the present invention as any other layer than the light-emitting layer therein. For example, the film containing the organic-inorganic perovskite may be used as the above-mentioned hole transport layer or electron transport layer. In that case, the organic-inorganic perovskite of the film for use as the light-emitting layer and the organic-inorganic perovskite of the film for use as the other layer than the light-emitting layer may be the same or different.

In producing the electroluminescent device, the organic layers constituting the electroluminescent device are sequentially layered on the support. The film formation method for forming these layers is not specifically limited, and the layers may be formed according to any of a dry process or a wet process. For the film formation method for forming the light-emitting layer, reference may be made to the contents of the section of [Film Formation Method] given hereinabove.

Preferred materials for use for the electroluminescent device are concretely exemplified below. However, the materials for use in the present invention are not limitatively interpreted by the following exemplary compounds. Compounds, even though exemplified as materials having a specific function, can also be used as other materials having any other function.

First, preferred examples of compounds for use as a host material in the light-emitting layer are mentioned below.

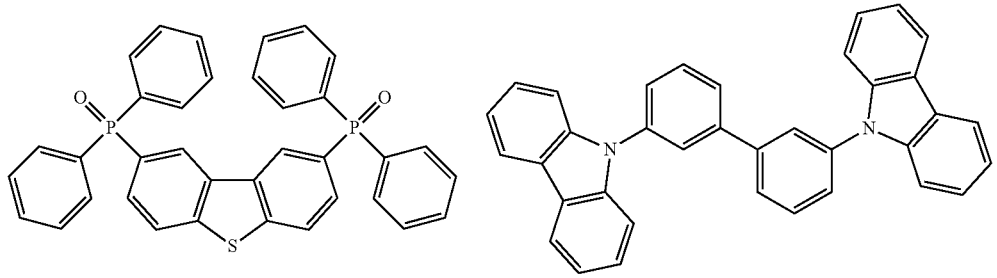

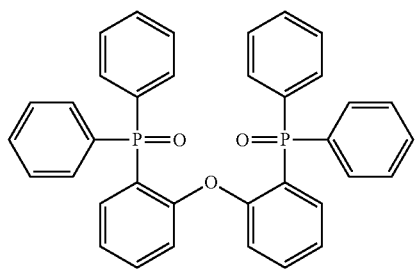

-continued
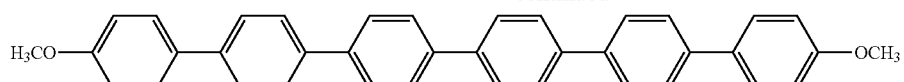
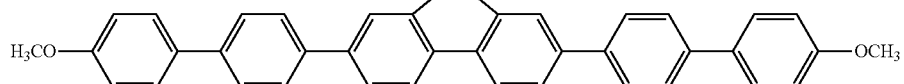
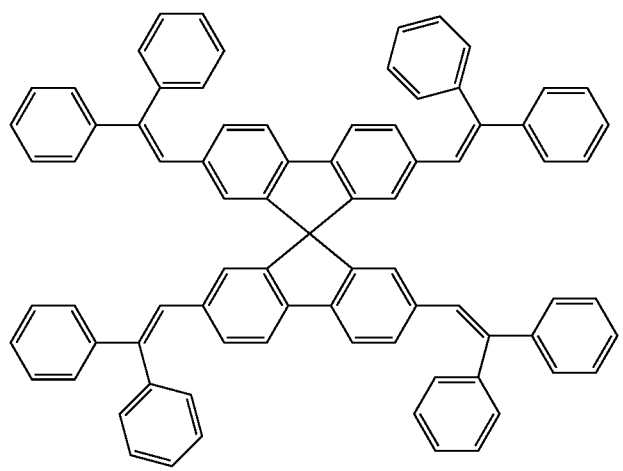
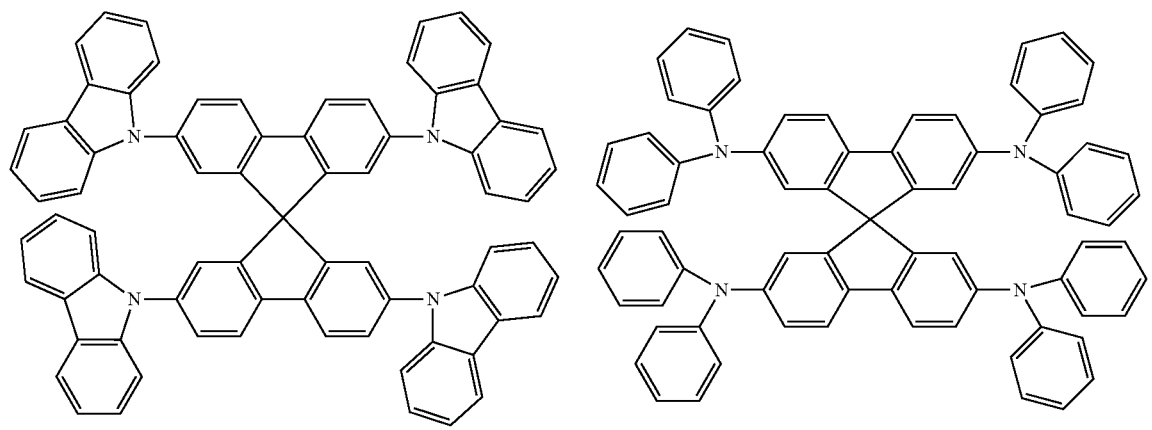
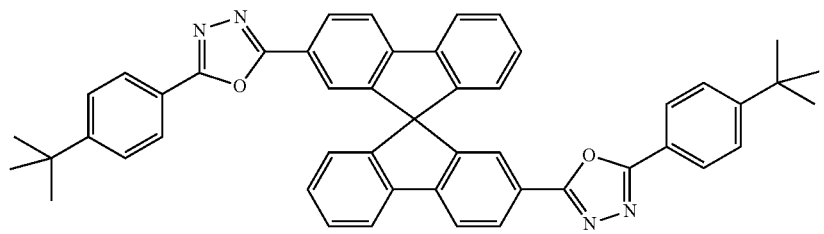

-continued
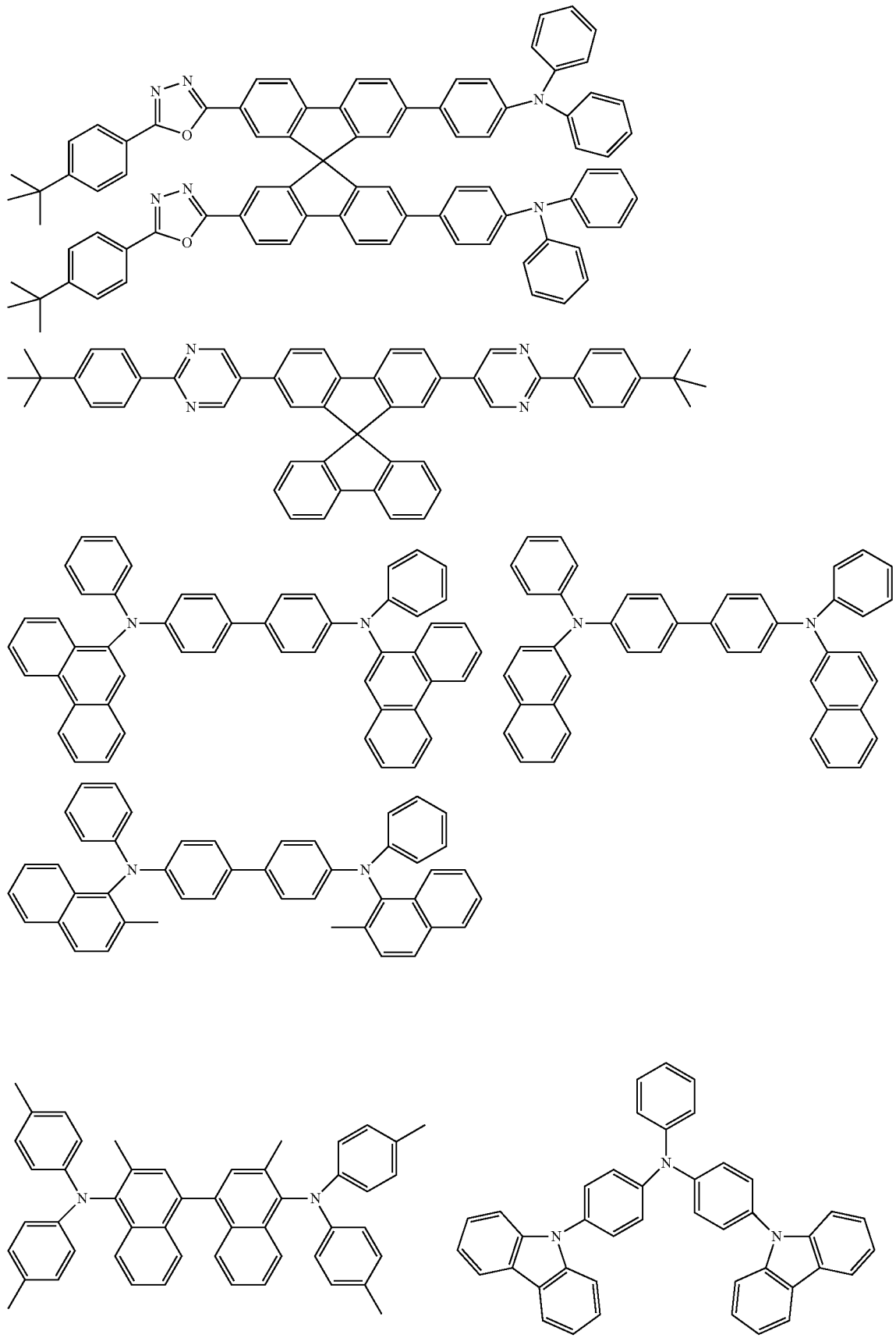

-continued
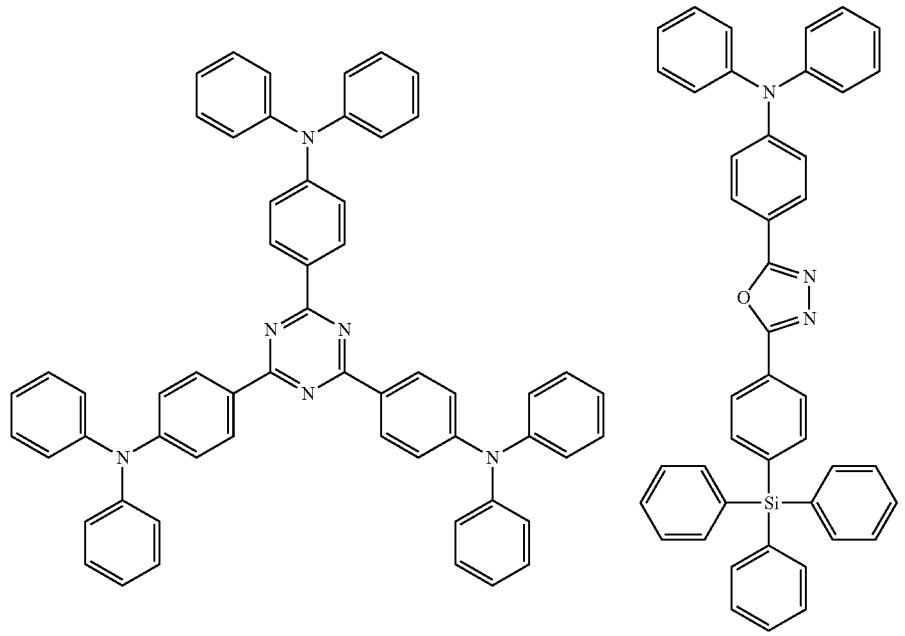
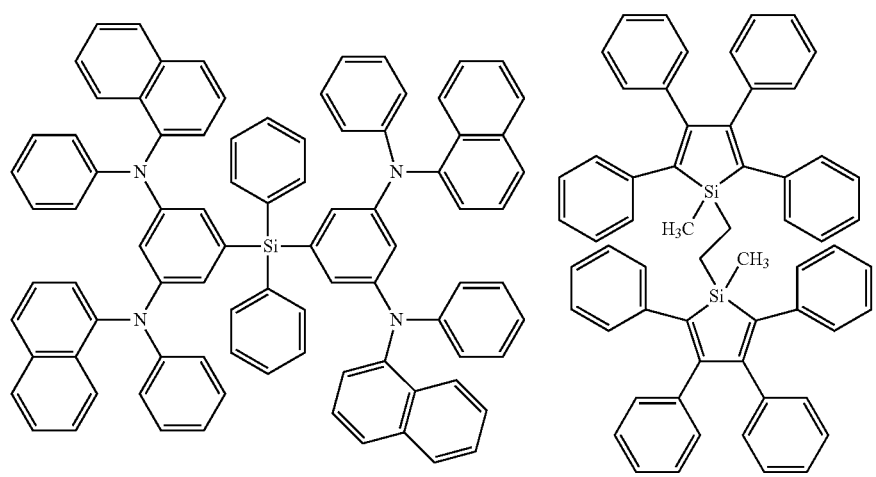
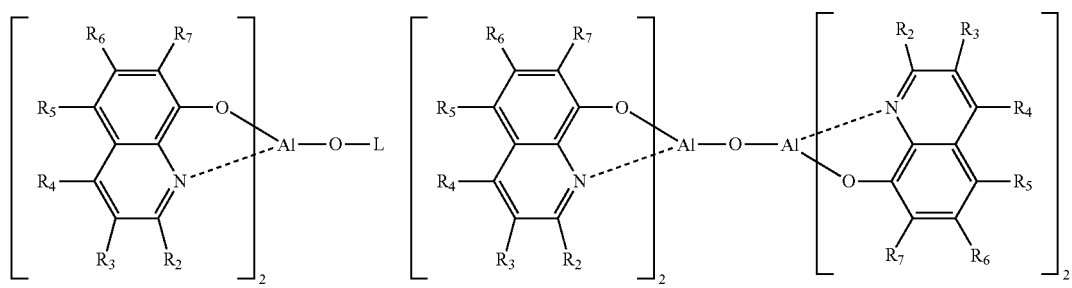
R₂-R₇ = H or substituent
L = Ligand
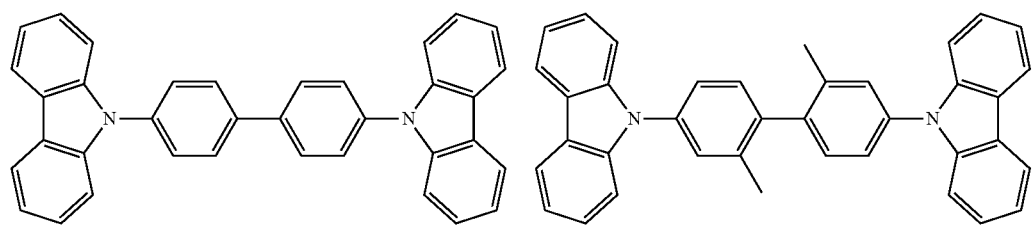

-continued
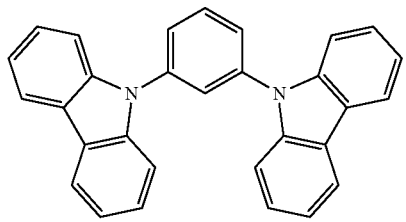
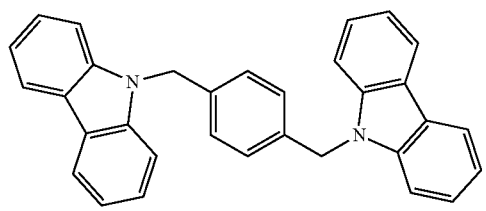
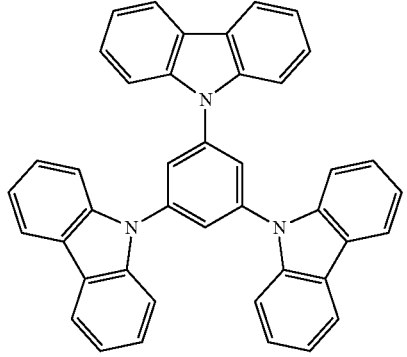
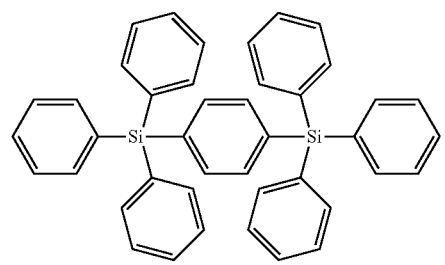
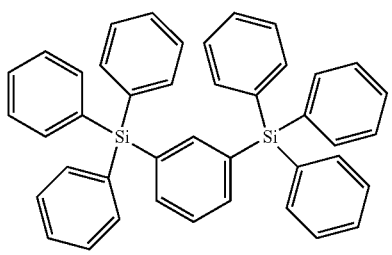
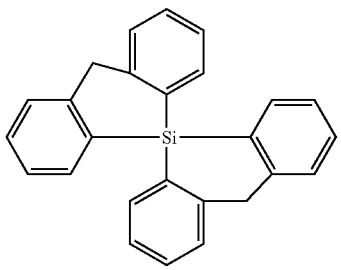
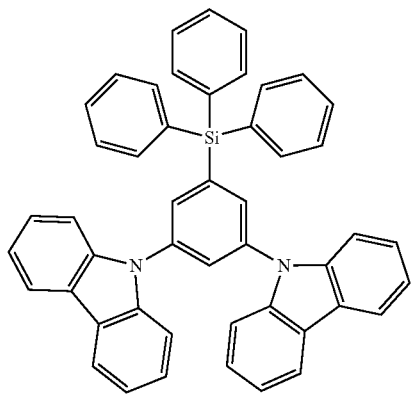
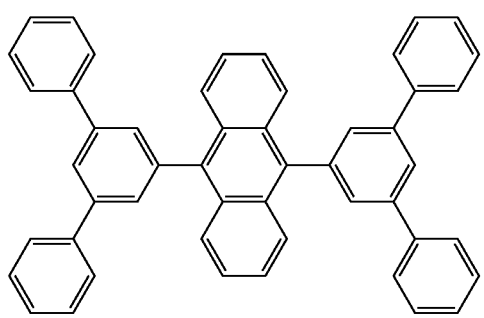
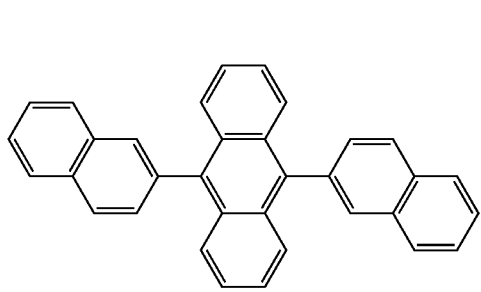
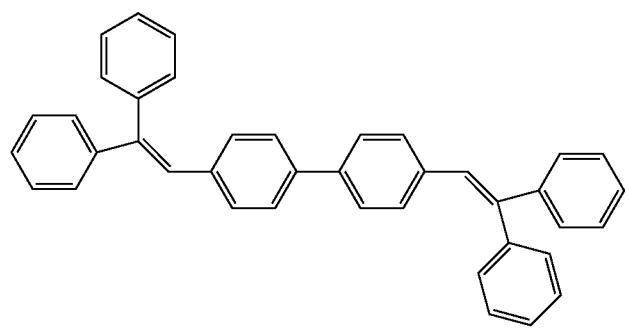

-continued
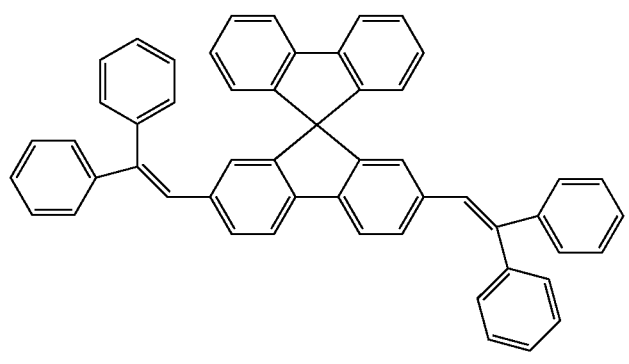
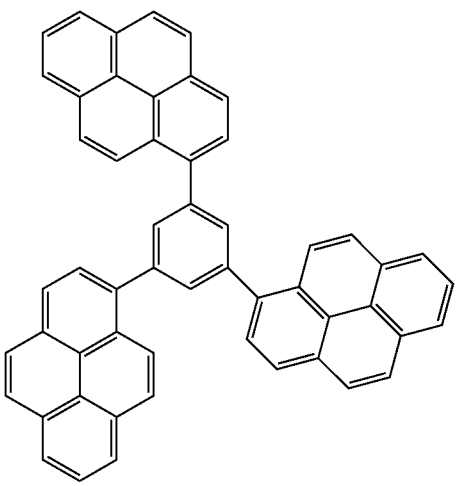
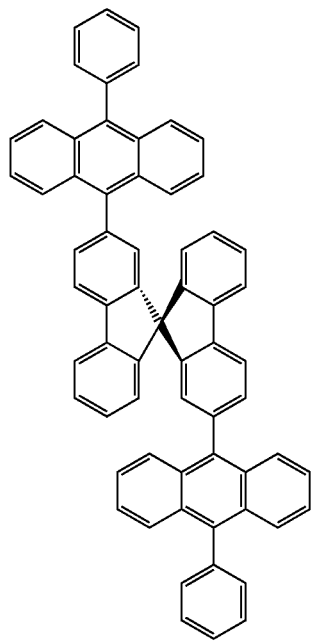
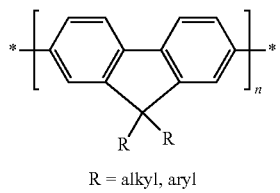
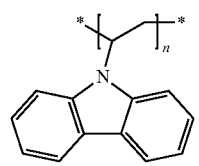
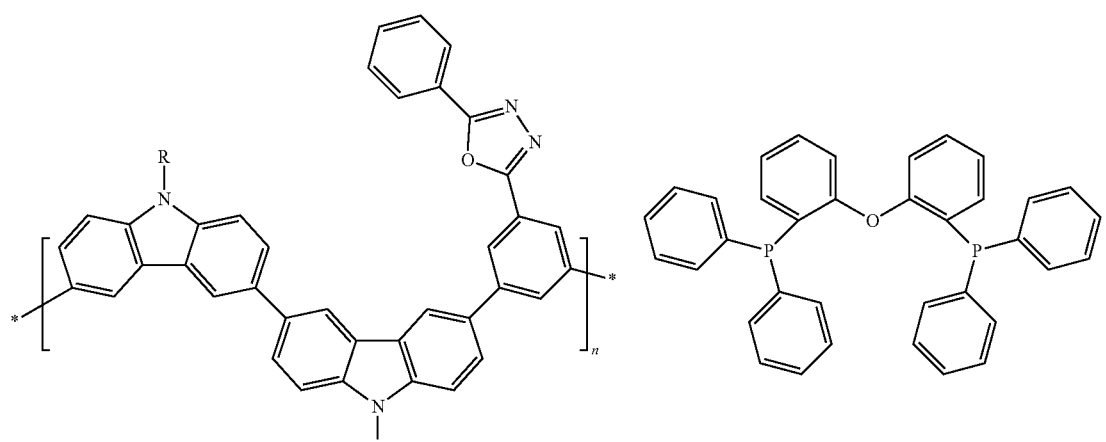

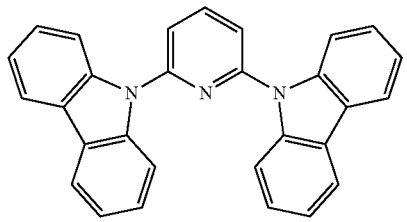
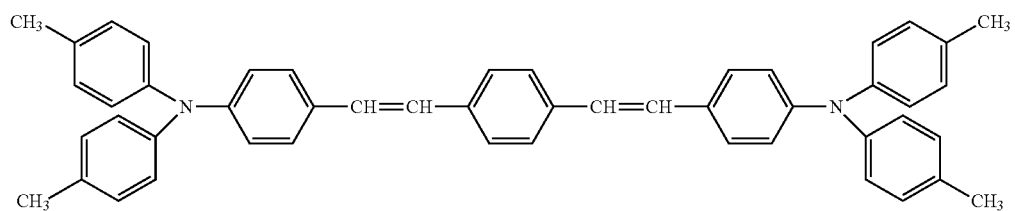
Next, preferred examples of compounds for use as a hole injection material are mentioned below.
$MoO_x$ where x is 1.5 to 3.0.
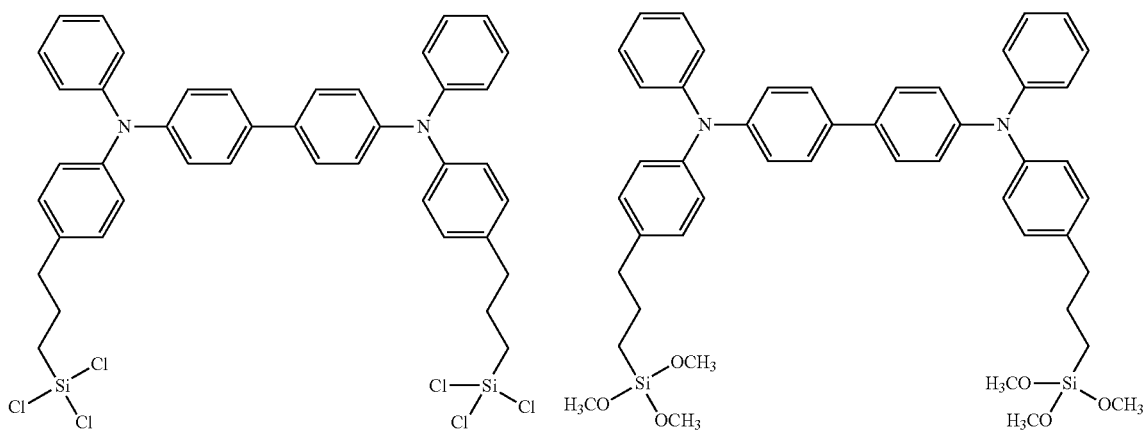
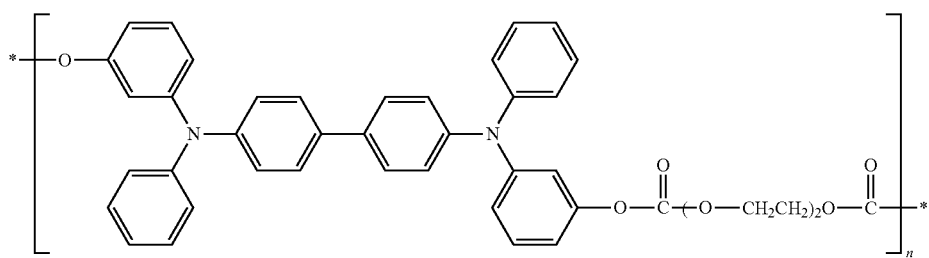

-continued
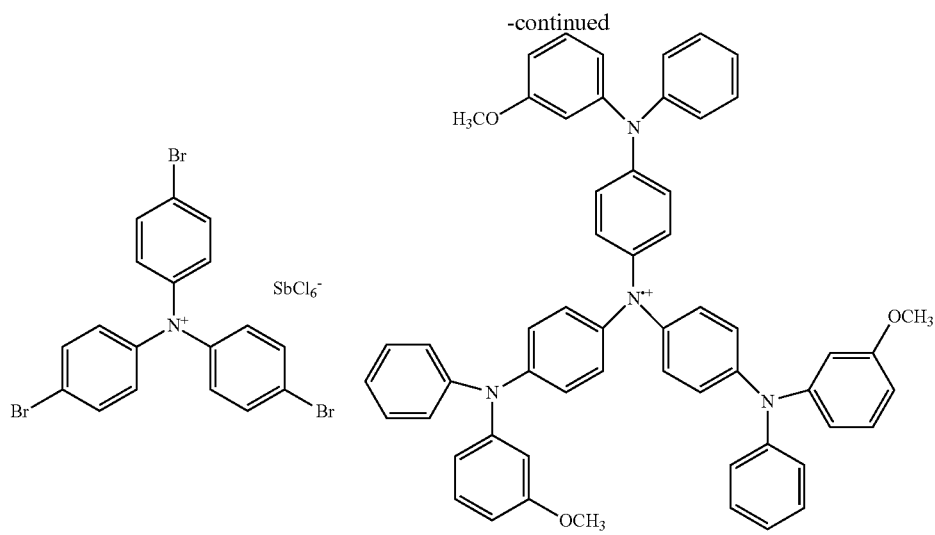
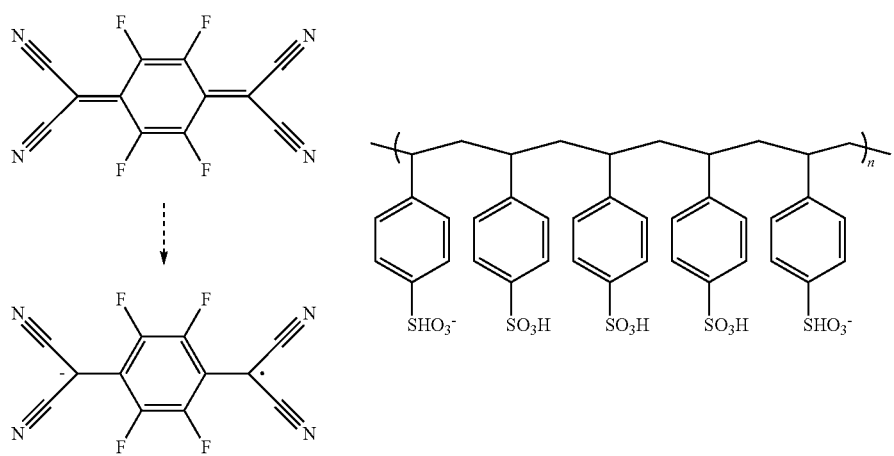
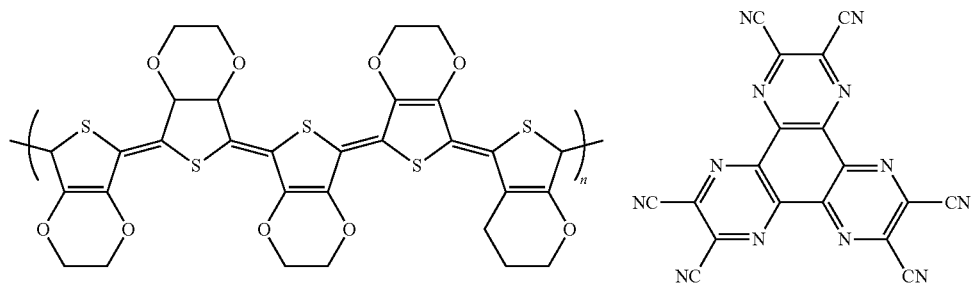

Next, preferred examples of compounds for use as a hole transport material are mentioned below.
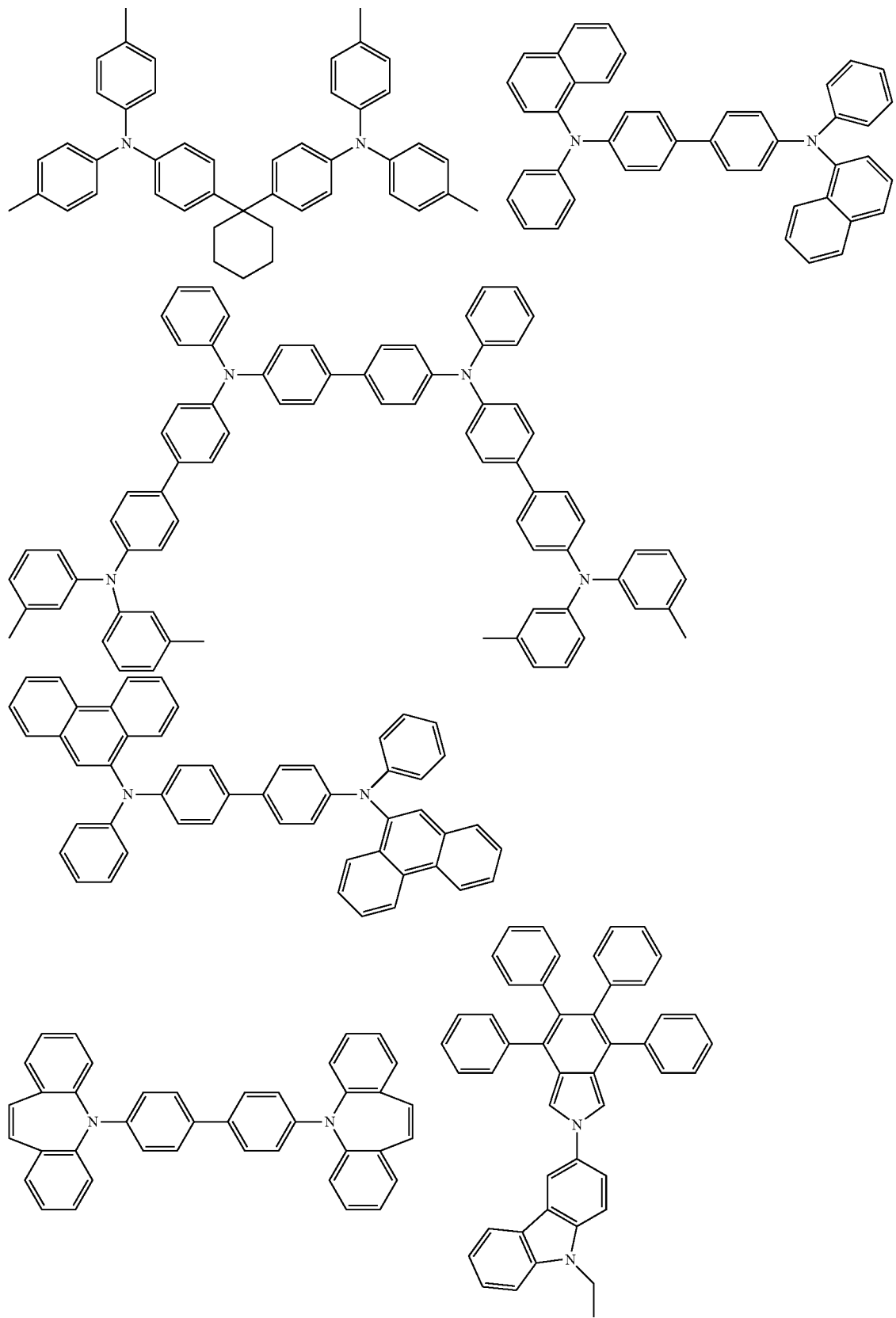

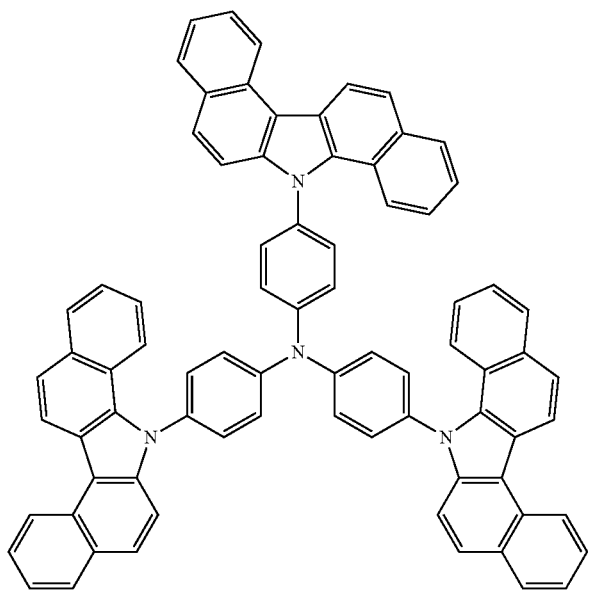
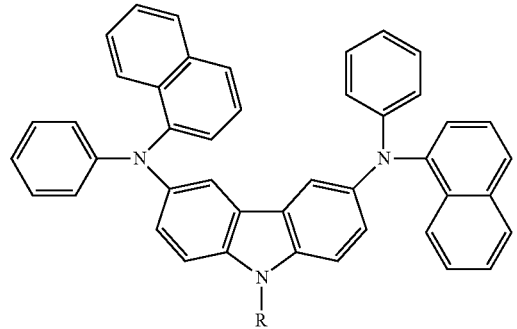
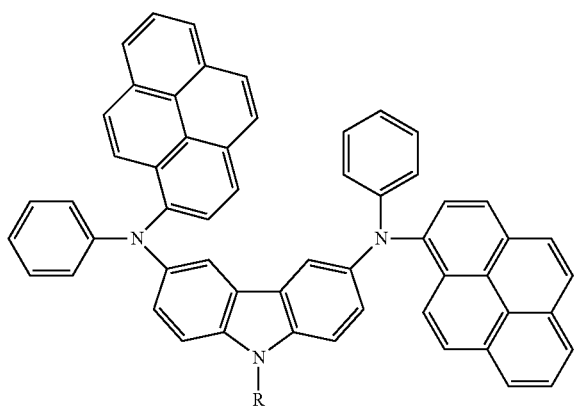
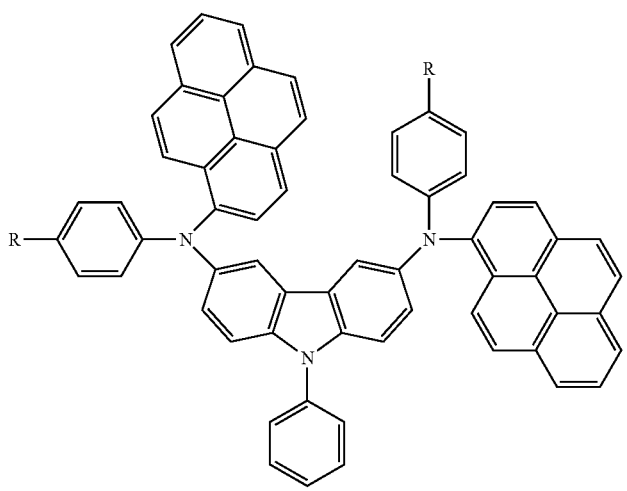

-continued
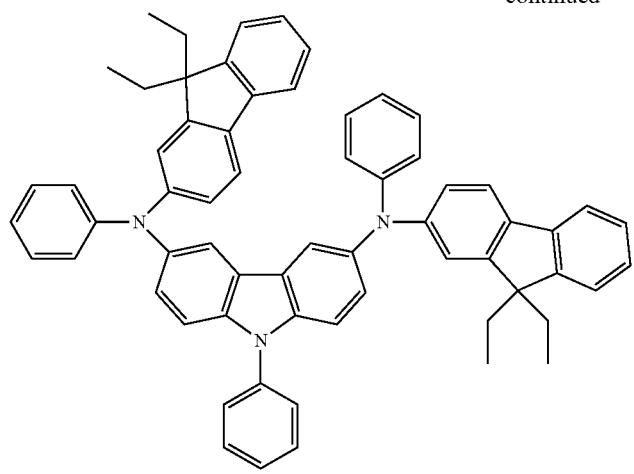
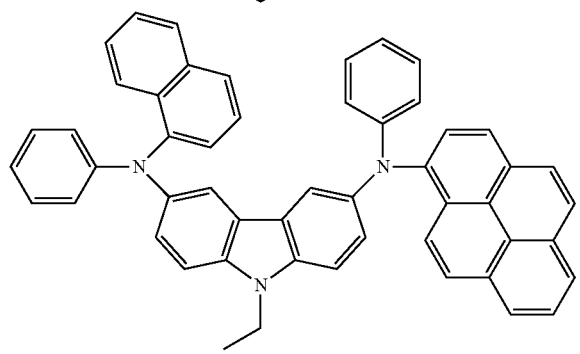
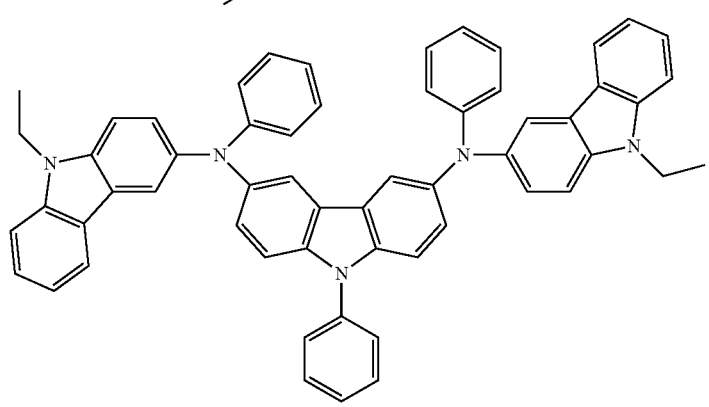
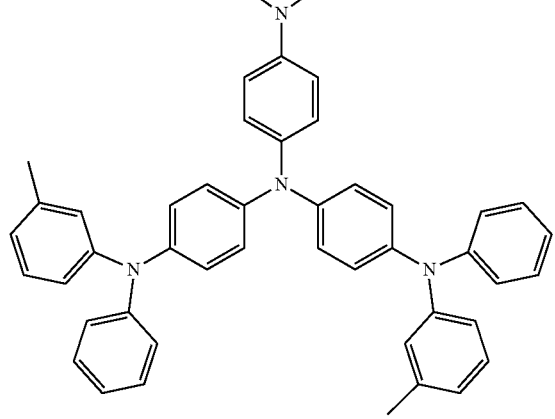
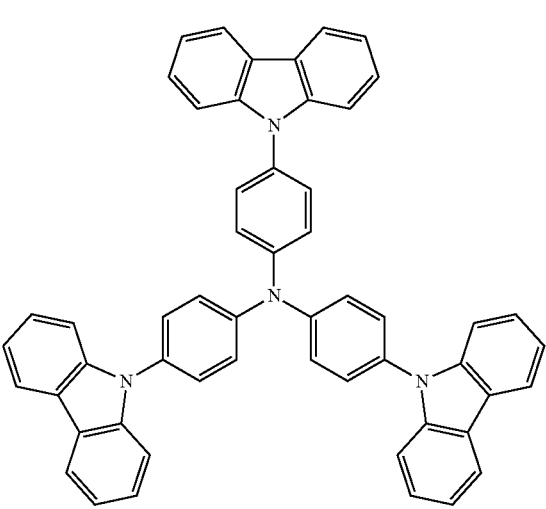

-continued
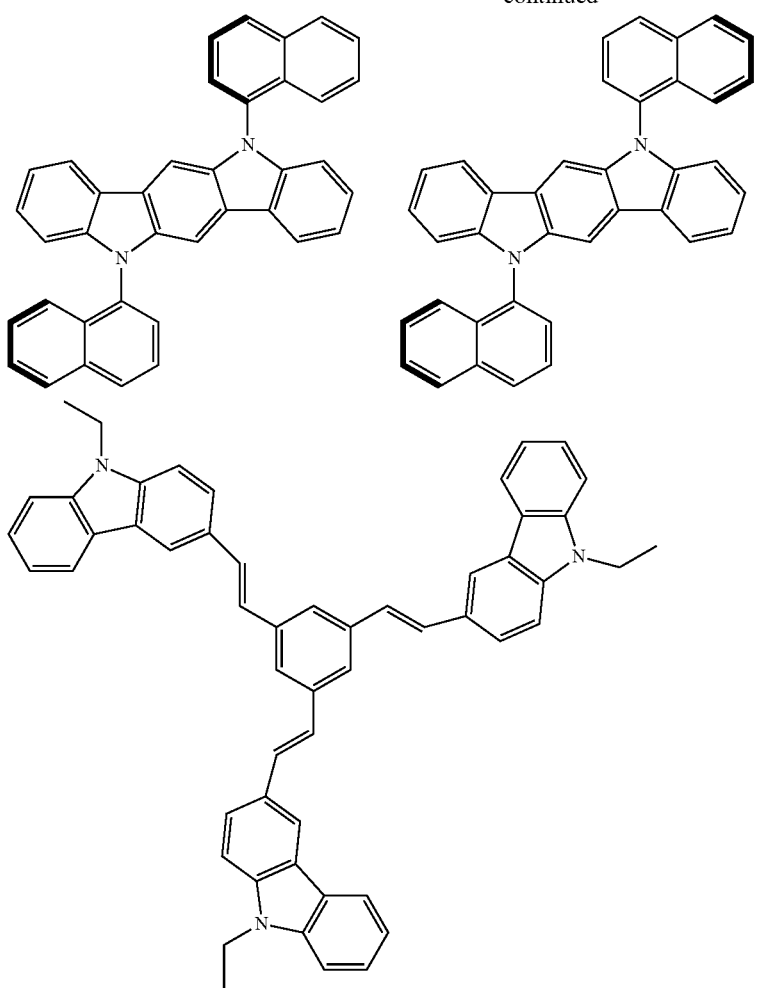
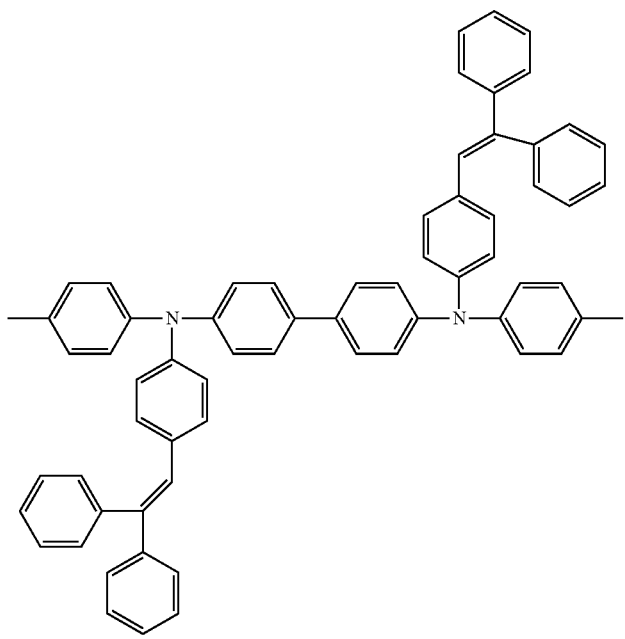

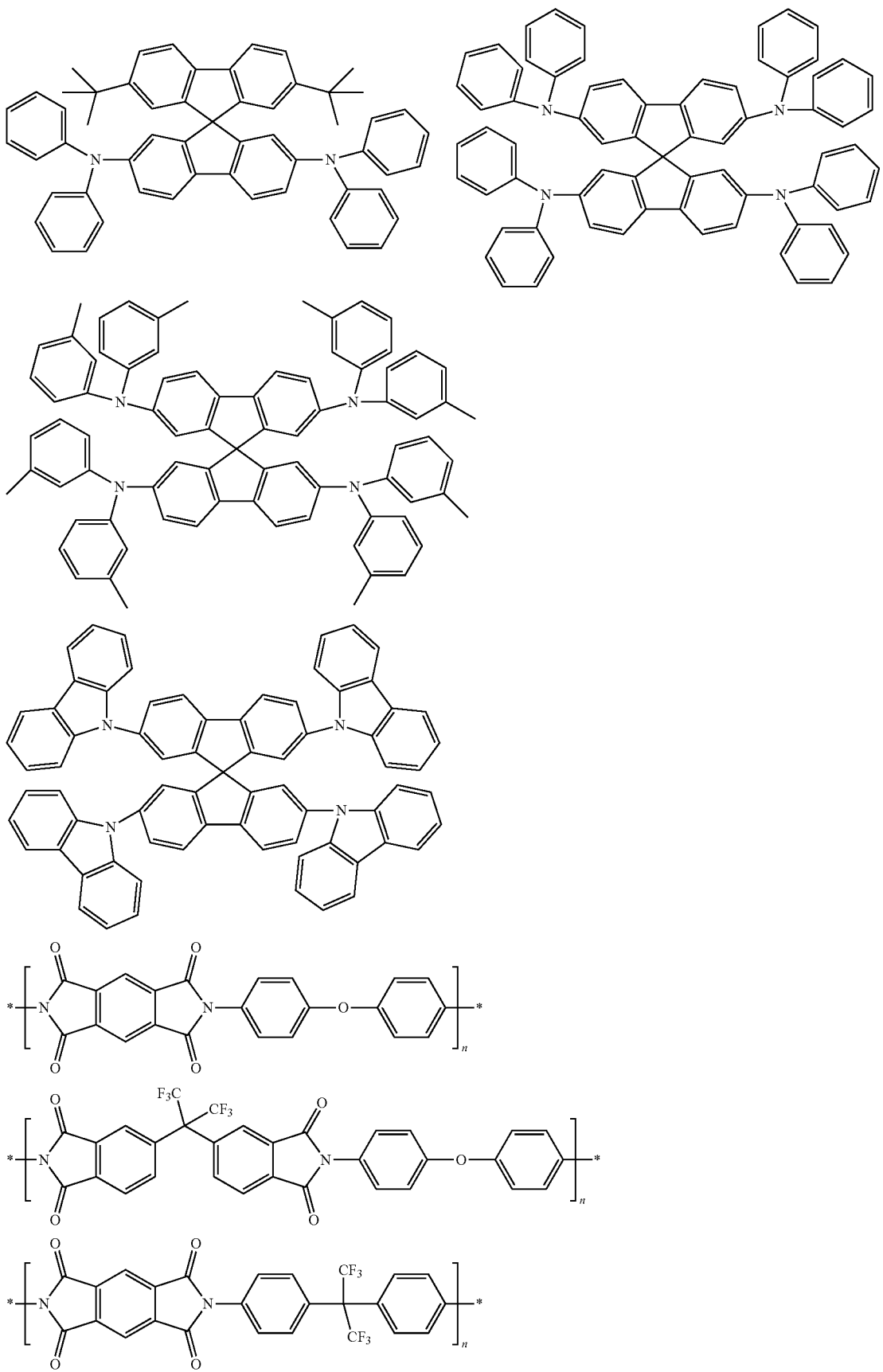

-continued
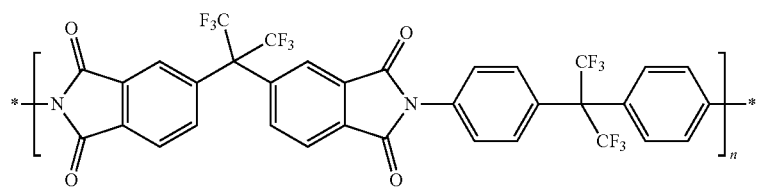
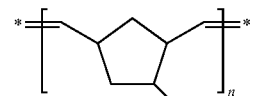
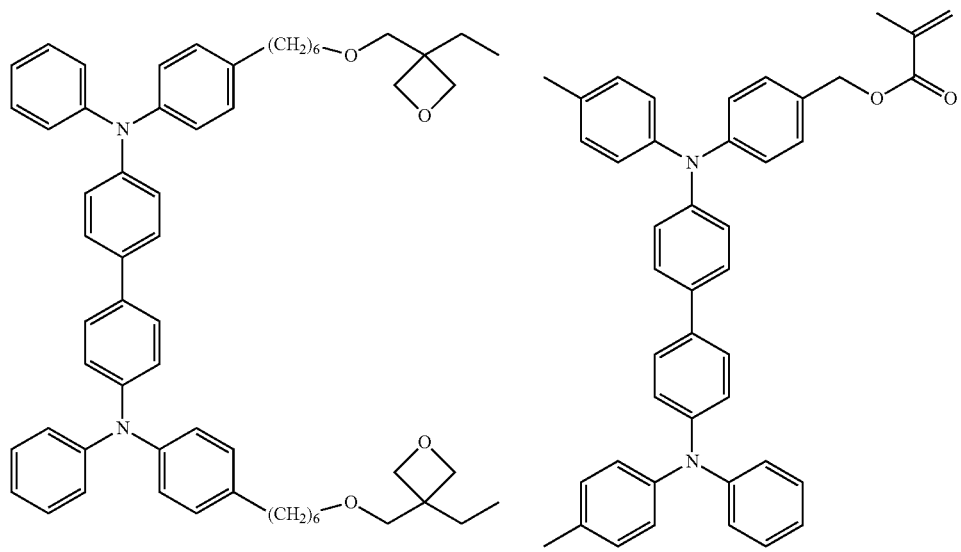
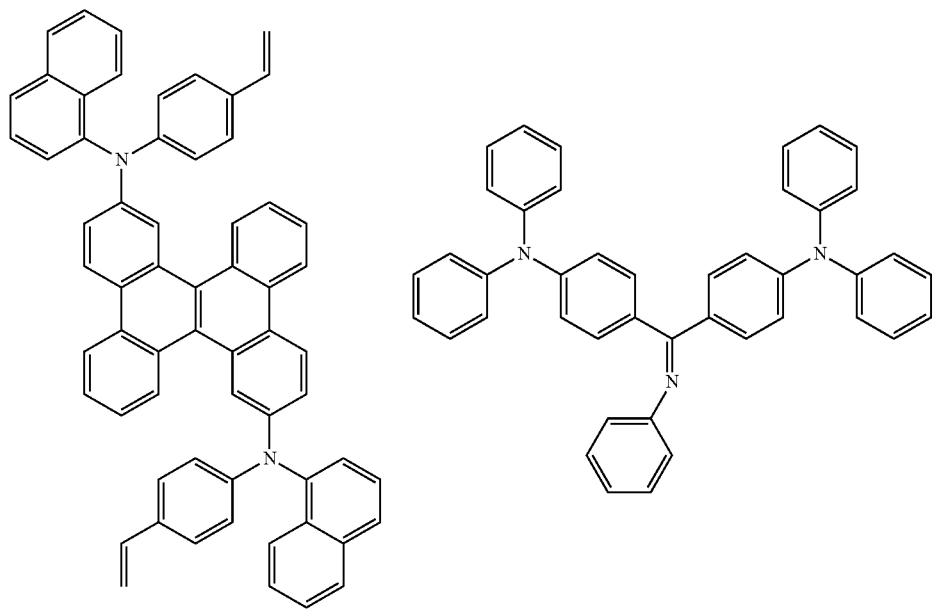

-continued
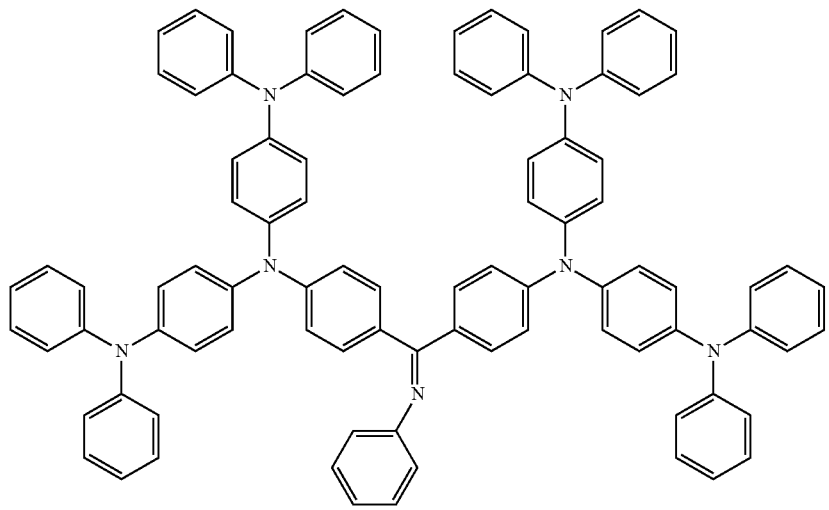
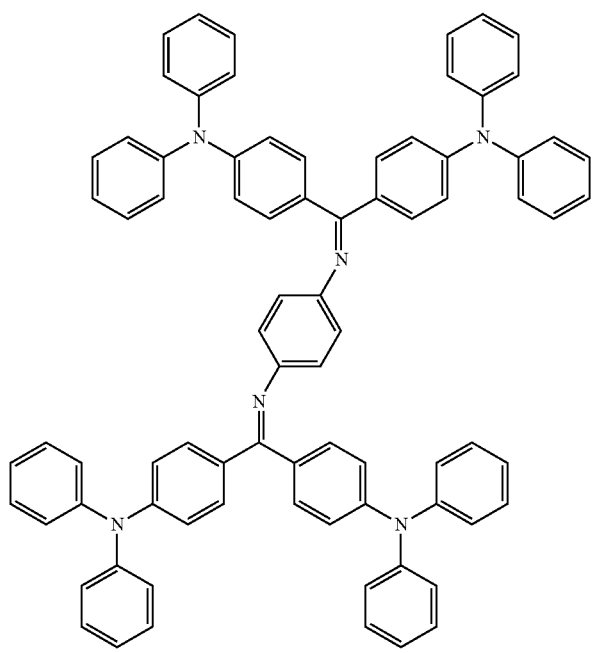

-continued
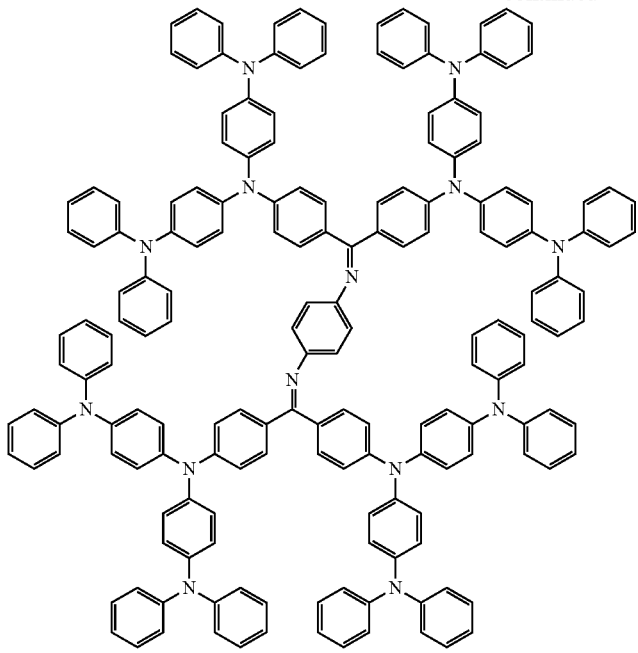
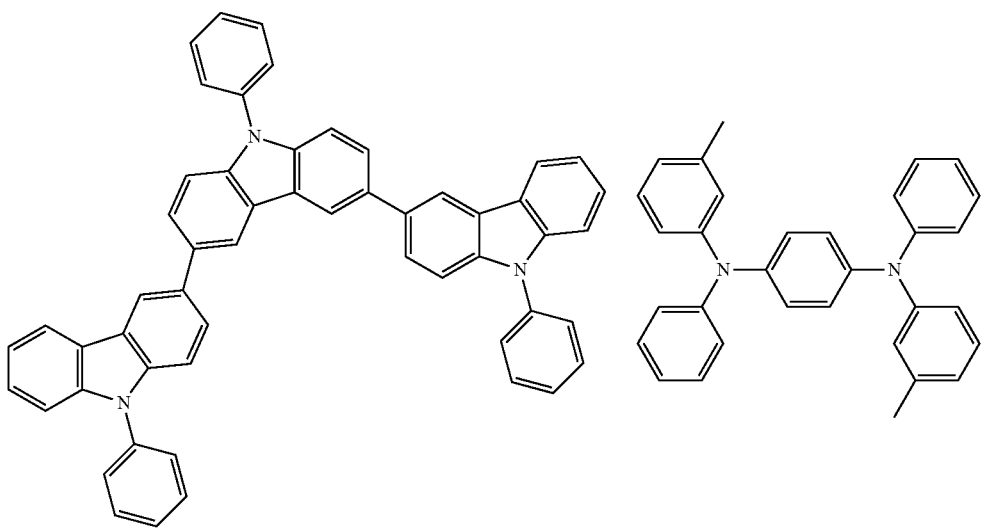
R = alkyl, aryl, alkoxy, aryloxy, 9,9′-dialkylfluorene Next, preferred examples of compounds for use as an electron blocking material are mentioned below.
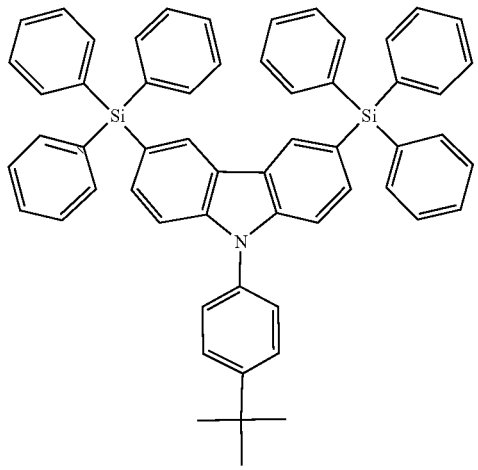
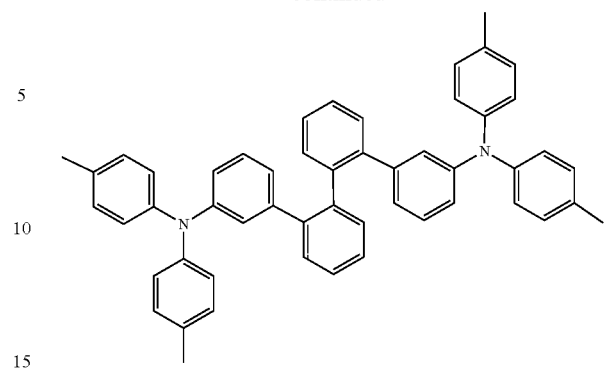
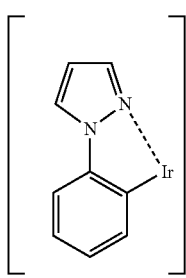
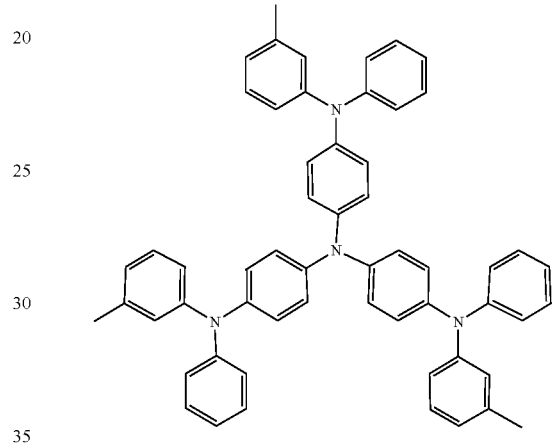
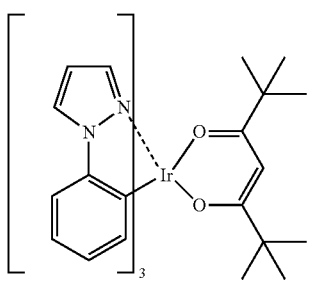
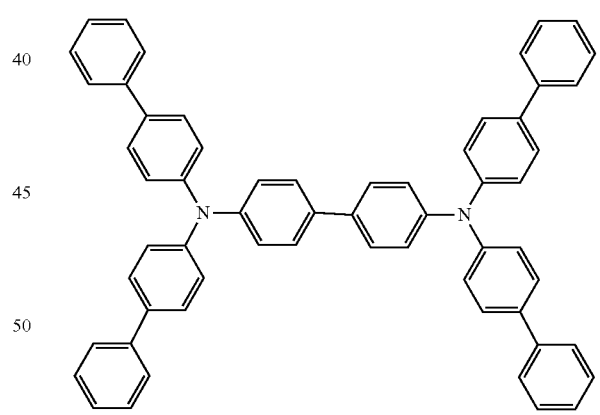
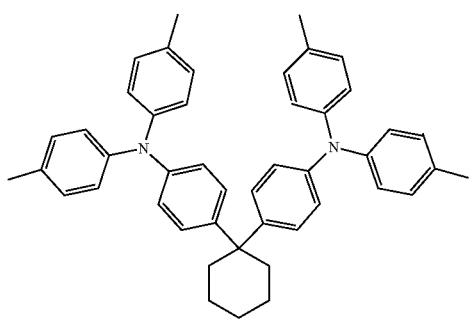
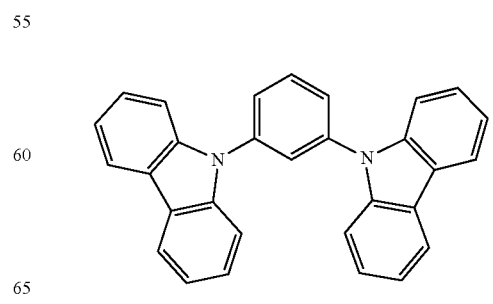

Next, preferred examples of compounds for use as a hole blocking material are mentioned below.
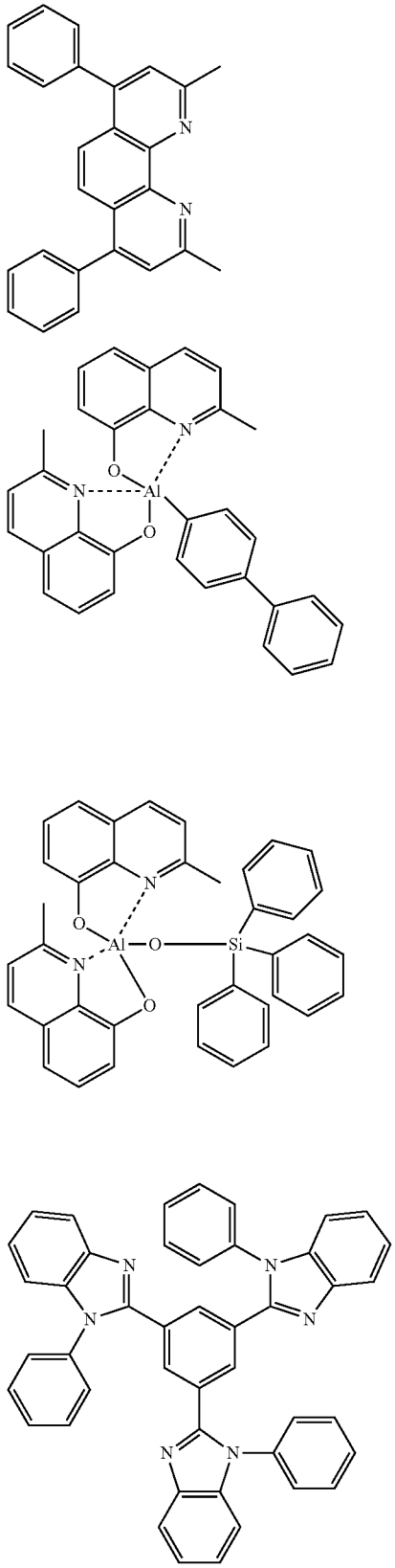
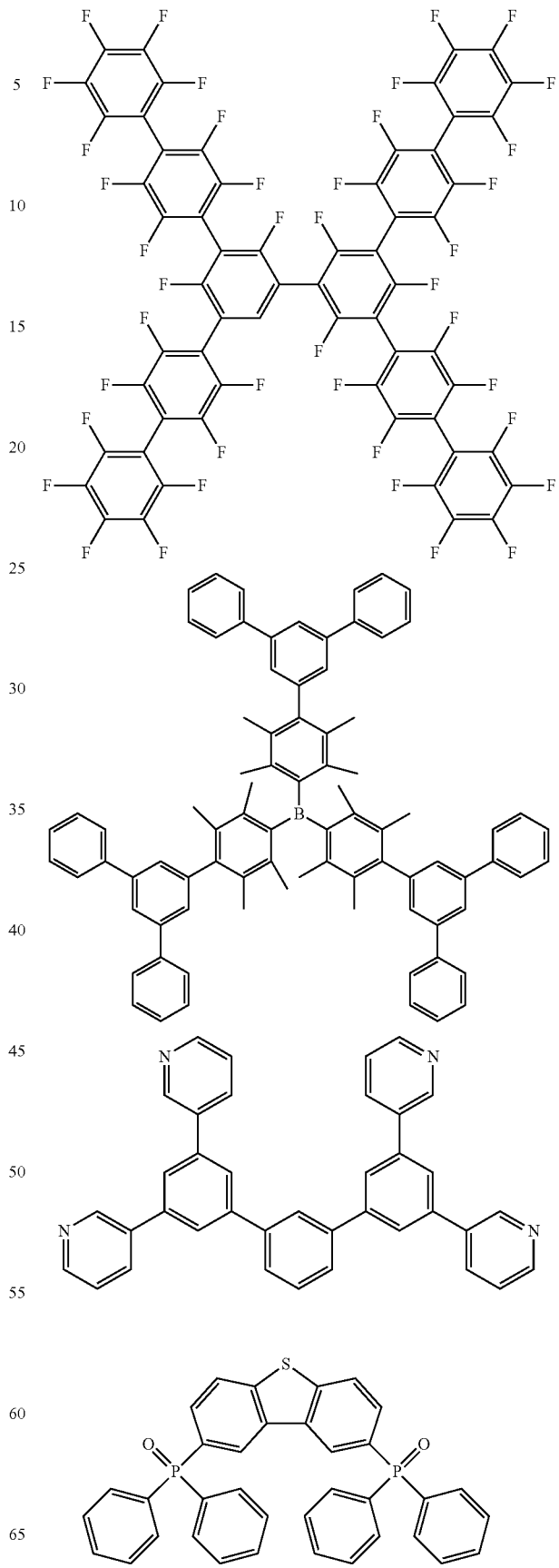

51
-continued
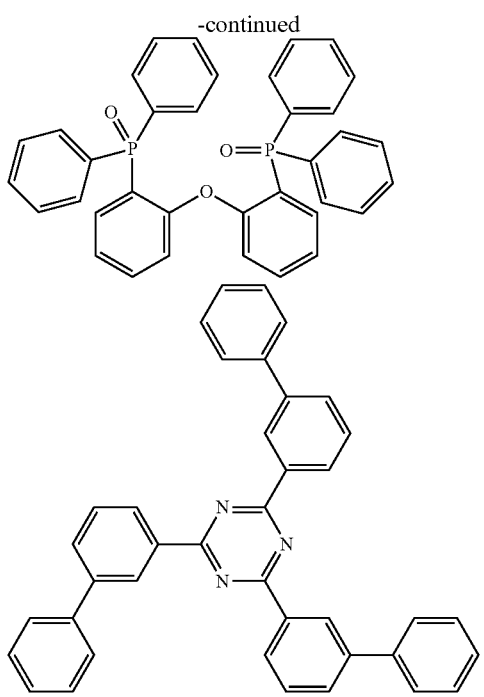
52
-continued
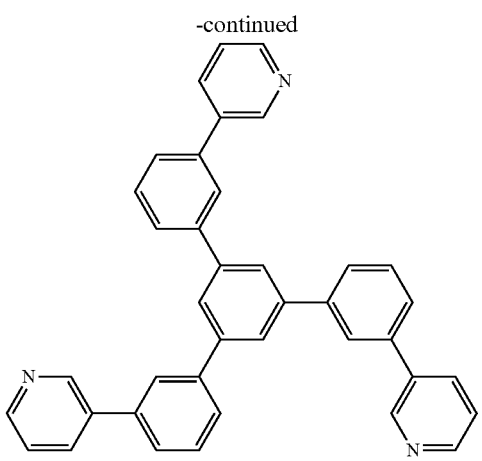
Next, preferred examples of compounds for use as an electron transport material are mentioned below.
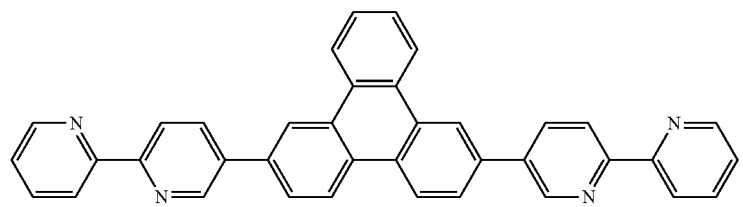
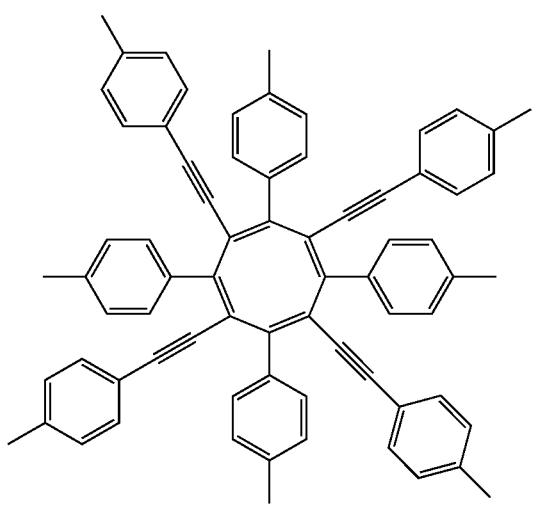

-continued
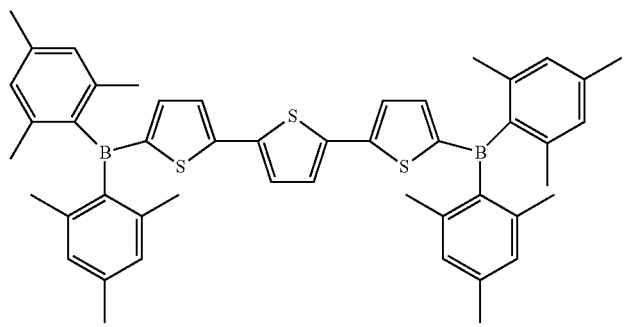
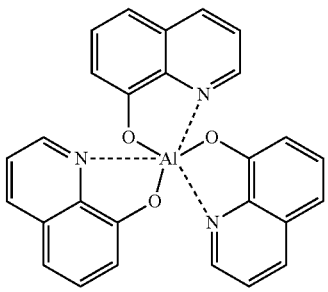
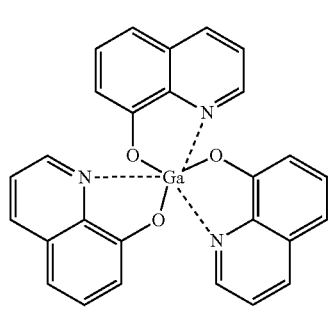
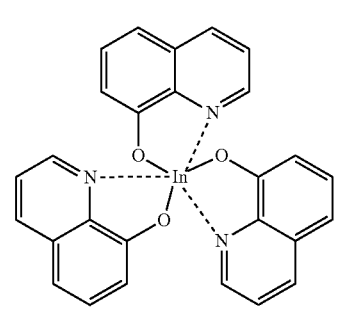
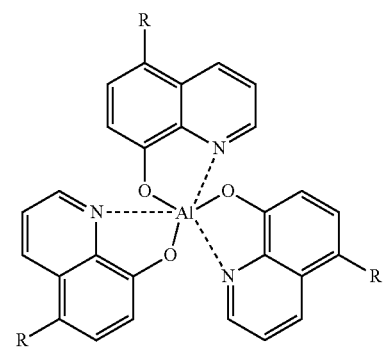
R = H, alkyl, aryl, heteroaryl
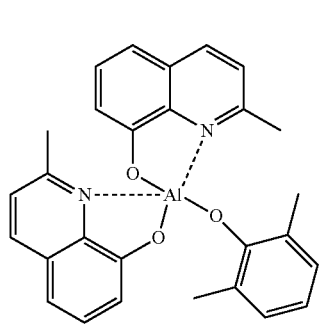
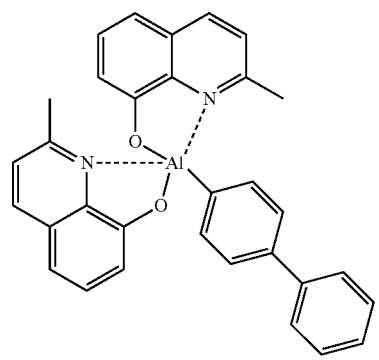
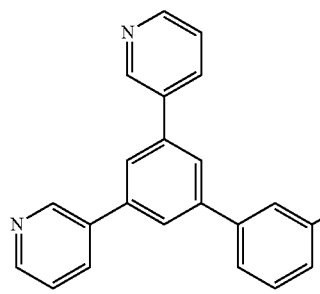
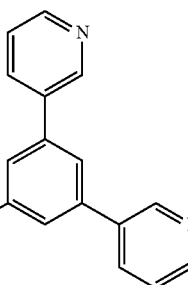
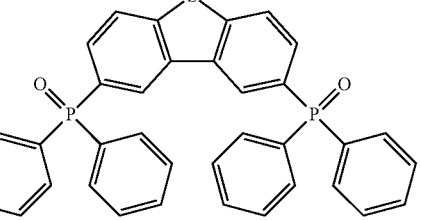
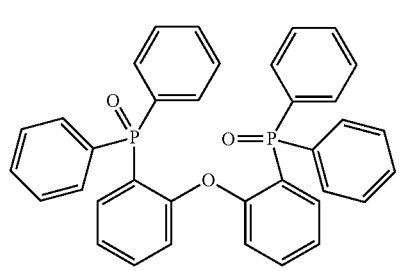
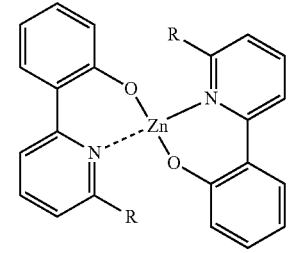
R = H
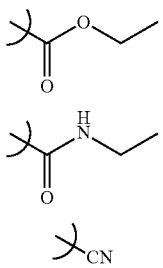

-continued
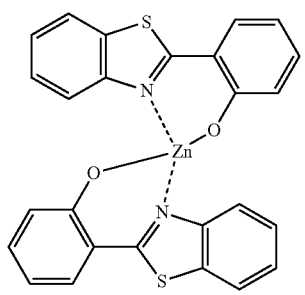
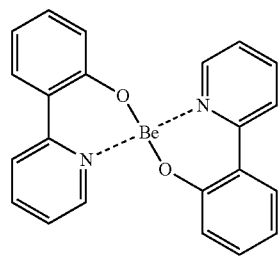
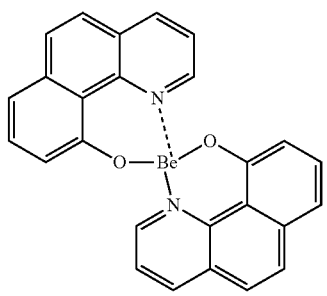
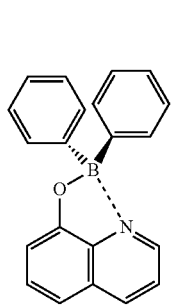
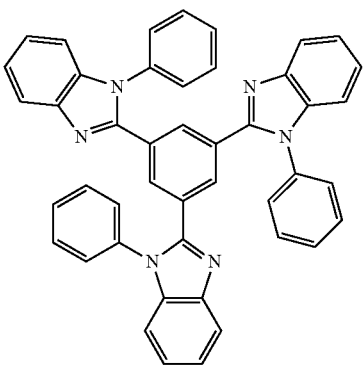
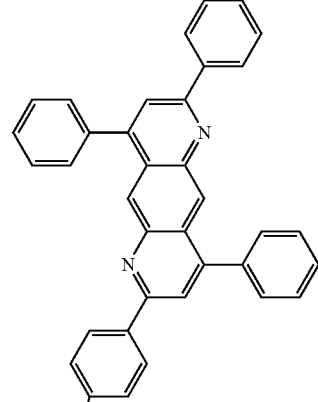
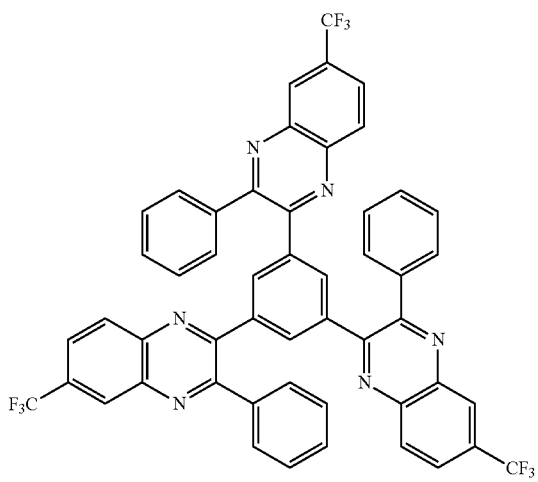
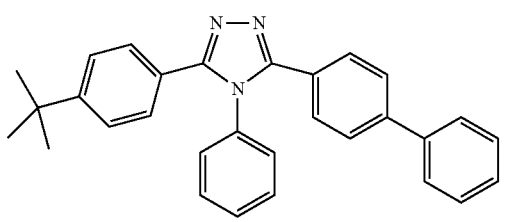
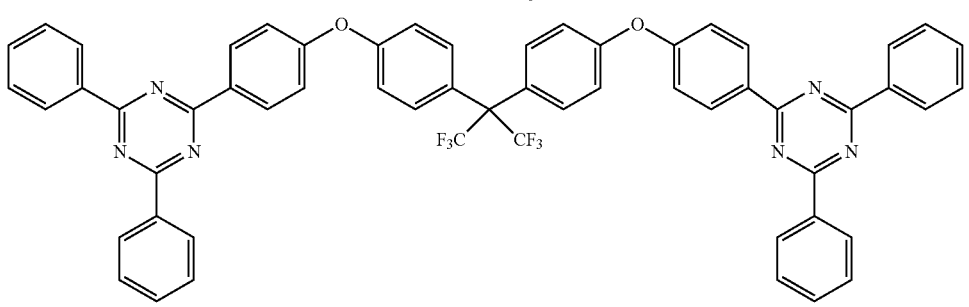

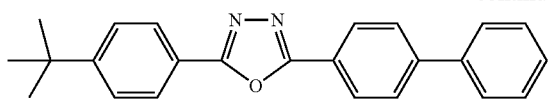
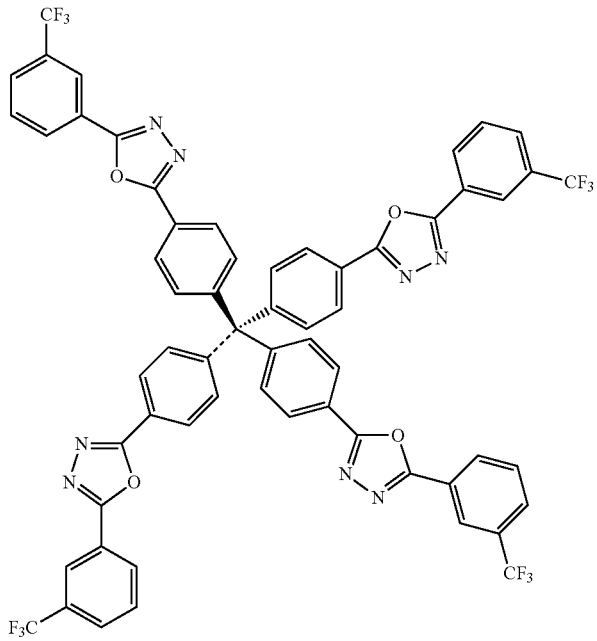
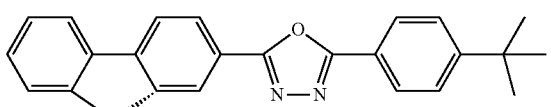
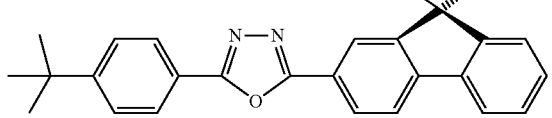
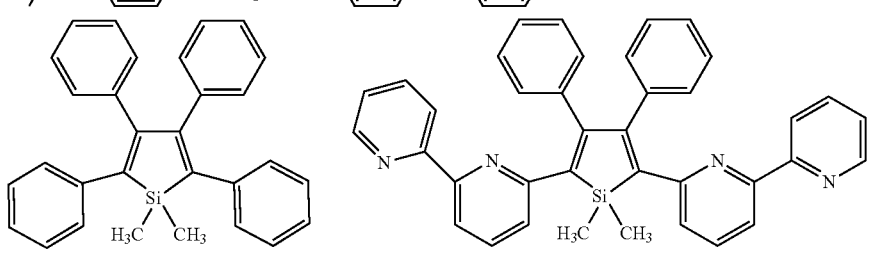
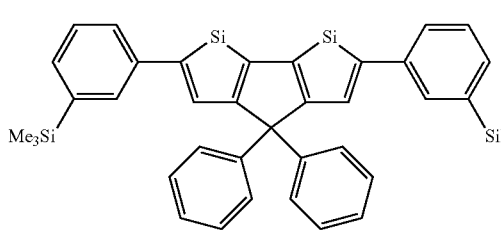
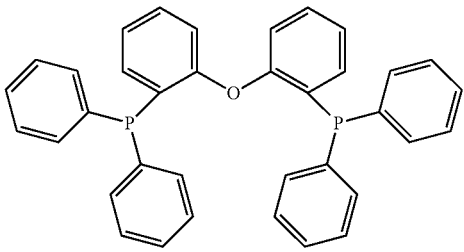
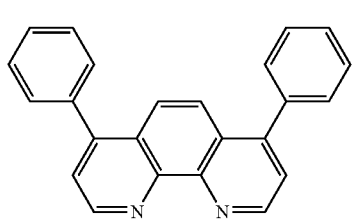
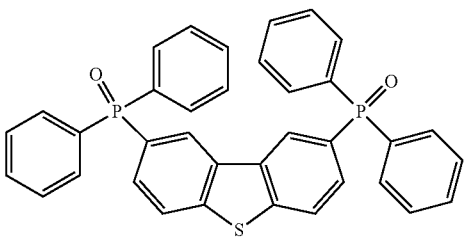

Next, preferred examples of compounds for use as an electron injection material are mentioned below.

LiF, CsF, Cs

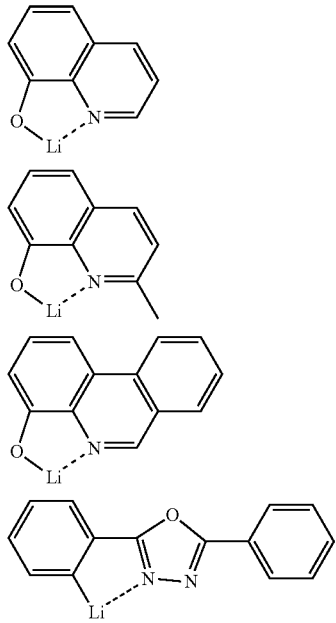

Further, preferred examples of compounds for use as additional materials are mentioned below. For example, these are considered to be added as a stabilization material.

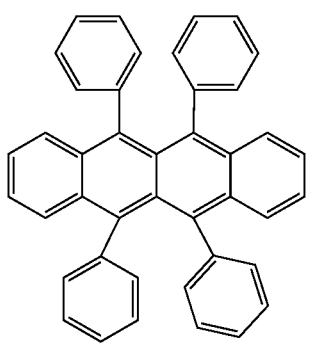

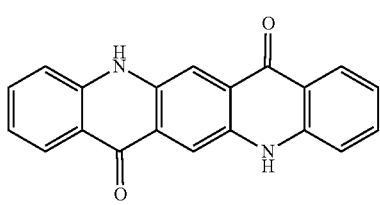

-continued

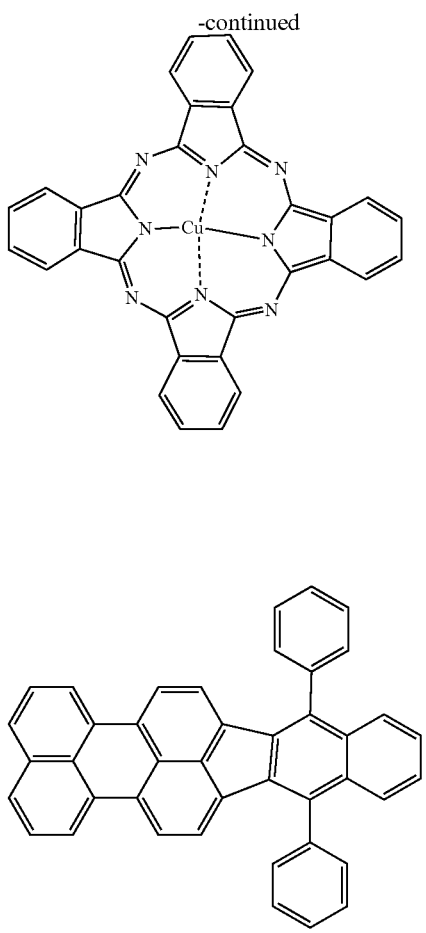

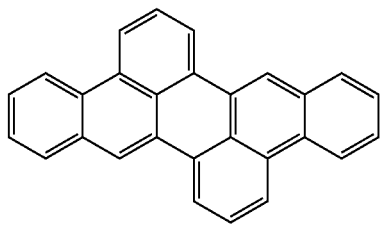

The electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with the organic-inorganic perovskite of the present invention at room temperature since the excited triplet energy is converted to heat or the like due to the instability thereof. The excited triplet energy of the organic-inorganic perovskite may be measured by observing light emission under an extremely low temperature condition.

<Production Method for Light-Emitting Device>

The method for producing a light-emitting device of the present invention is characterized in that an organic-inorganic perovskite is so planned as to satisfy the following requirements, and a light-emitting device is produced using the organic-inorganic perovskite satisfying the following requirements (1) and (2):

$$E_T < E_{T1} \quad (1)$$

$$E_S - E_T \leq 0.1 \text{ eV} \quad (2)$$

wherein $E_S$ represents the excited singlet energy level in emission of an inorganic component constituting the organic-inorganic perovskite, $E_T$ represents the excited triplet energy level in emission of an inorganic component constituting the organic-inorganic perovskite, $E_{S1}$ represents the excited singlet energy level in emission of an organic component constituting the organic-inorganic perovskite and $E_{T1}$ represents the excited triplet energy level in emission of an organic component constituting the organic-inorganic perovskite.

For the description of the requirements (1) and (2), the definitions of $E_S$, $E_T$, $E_{S1}$, and $E_{T1}$, and the measurement methods and the preferred ranges thereof, reference may be made to the corresponding description on the section of "Organic-Inorganic Perovskite>given hereinabove; and for the configuration of the light-emitting device to be produced and the other step than the planning step for the organic-inorganic perovskite, reference may be made to the corresponding description in the section of <Light-Emitting Device>.

The organic-inorganic perovskite can be planned, for example, by selecting and combining the ions and the number of n for R, A, B and X in the formula (10) so as to satisfy the requirements (1) and (2). As described above, the organic-inorganic perovskite satisfying the requirements (1) and (2) have a high emission efficiency, and therefore according to the production method, a light-emitting device using the organic-inorganic perovskite having a high emission efficiency can be produced at a low cost.

The electroluminescent device of the invention may be applied to any of a single device, a structure with plural devices disposed in an array, and a structure having anodes and cathodes disposed in an X-Y matrix. According to the present invention using a film containing the organic-inorganic perovskite of the present invention as a light-emitting layer, a light-emitting device having a markedly improved light emission efficiency can be obtained. The light-emitting device such as the electroluminescent device of the present invention may be applied to a further wide range of purposes. For example, an electroluminescent display apparatus may be produced with the electroluminescent device of the invention, and for the details thereof, reference may be made to S. Tokito, C. Adachi and H. Murata, "Yuki EL Display" (Organic EL Display) (Ohmsha, Ltd.). In particular, the electroluminescent device of the invention may be applied to electroluminescent illumination and backlight which are highly demanded.

EXAMPLES

The features of the present invention will be described more specifically with reference to Examples given below. The materials, processes, procedures and the like shown below may be appropriately modified unless they deviate from the substance of the invention. Accordingly, the scope of the invention is not construed as being limited to the specific examples shown below. For measurement of photoabsorption spectra, used was a UV-visible-near IR spectrophotometer (Lambda 950-PKA, Perkin Elmer); for measurement of emission spectra, used was a measurement device (Fluoromax-4, Horiba Jobin, Yvon); for measurement of transient decay curves of emission, used was a streak camera (C4334, Hamamatsu Photonics); for X-ray diffraction analysis, used was an X-ray diffractometer (RINT-2500, Rigaku); for measurement of electroluminescent device characteristics, used were an external quantum efficiency measurement device ($C_{9920}$-12, Hamamatsu Photonics), Source Meter (2400 series, Keithley Instruments), and a multichannel analyzer (PMA-12, Hamamatsu Photonics); and for measurement of film thickness, used was a profile meter (DektakXT, Bruker).

The organic-inorganic perovskite used in the following Examples 1 and 2 is $PEA_2FA_{n-1}Pb_nBr_{3n+1}$ (n=8). Here, PEA represents a phenylethylammonium, and FA represents a formamidinium. The organic-inorganic perovskite used in the Comparative Examples 1 and 2 is $NMA_2FA_{n-1}Pb_nBr_{3n+1}$ (n=8). Here, NMA represents a 1-naphthylmethylammonium, and FA represents a formamidinium. The excited singlet energy level $E_S$ and the excited triplet energy level $E_T$ in emission of the inorganic component constituting each perovskite and the excited singlet energy level $E_{S1}$ and the excited triplet energy level $E_{T1}$ in emission of the organic component constituting each perovskite are shown in Table 1.

TABLE 1

| Organic-Inorganic Perovskite | Inorganic Component | | Organic Component | |
|---|---|---|---|---|
| | excited singlet energy level in emission $E_S$ | excited triplet energy level in emission $E_T$ | excited singlet energy level in emission $E_{S1}$ | excited triplet energy level in emission $E_{T1}$ |
| $PEA_2FA_{n-1}Pb_nBr_{3n+1}$ (n = 8) | 3.01 eV | 2.99 eV | 4.4 eV | 3.3 eV |
| $NMA_2MA_{n-1}Pb_nBr_{3n+1}$ (n = 8) | 3.01 eV | 2.99 eV | 4.1 eV | 2.6 eV |

(Example 1) Production of Photoluminescent Device Using PEA-FA Perovskite Film

In a glove box in a nitrogen atmosphere, a film of $PEA_2FA_{n-1}Pb_nBr_{3n+1}$ (where n=8) was formed (hereinafter referred to as "PEA-FA perovskite film"). First, to an N,N-dimethylformamide solution of formamidinium bromide ($HC(NH_2)_2Br$) and lead bromide ($PbBr_2$) dissolved therein at a molar ratio of 1/1, 25 mol % of phenylethylammonium bromide ($C_6H_5CH_2CH_2NH_3Br$) was added to prepare a precursor solution having a PEA-FA perovskite concentration of 0.4 M. 50 μL of the PEA-FA perovskite precursor solution was dropwise applied onto a quartz glass substrate, and spin-coated at 4500 rpm for 30 seconds to form a PEA-FA perovskite precursor film. During the spin-coating, 0.3 mL of toluene was dropwise applied onto the film. Subsequently, the PEA-FA perovskite precursor film was baked at 70° C. for 15 minutes, and further baked at 100° C. for 5 minutes to form a PEA-FA perovskite film having a thickness of 150 nm, thereby providing a photoluminescent device.

(Comparative Example 1) Production of Photoluminescent Device Using NMA-FA Perovskite Film A photoluminescent device was produced in the same manner as in Example 1, except that, in forming the perovskite film, a film of $NMA_2FA_{n-1}Pb_nBr_{3n+1}$ was formed (hereinafter referred to a "NMA-FA perovskite film) using 1-naphthylmethylammonium bromide ($C_{10}H_7CH_2NH_3Br$) in place of phenylethylammonium bromide.

Each perovskite formed in Example 1 and Comparative Example 1 was analyzed to measure the X-ray diffraction spectrum thereof, and was confirmed to have a quasi-2D perovskite crystal structure.

FIG. 3 shows photoabsorption spectra measured at 300 K and emission spectra measured with a 450 nm excitation light of the perovskite films formed in Example 1 and Comparative Example 1; FIG. 4 is a graph showing excitation light intensity dependence of the photoluminescence quantum yield (PLQY) thereof; FIG. 5 shows transient decay curves of emission thereof with a 337 nm excitation light, measured at 30 K and 300 K; FIG. 6 shows transient decay curves of emission with a 337 nm excitation light, measured at 100 K, 200 K and 300 K, of the PEA-EA perovskite film formed in Example 1; FIG. 7 shows transient decay curves of emission with a 337 nm excitation light, measured at 100 K, 200 K and 300 K, of the NMA-FA perovskite film formed in Comparative Example 1.

As in FIG. 3, the PEA-FA perovskite film formed in Example 1 and the NMA-FA perovskite film formed in Comparative Example 1 have the same absorption characteristic with no absorption peak derived from low-dimensional perovskite particles, from which it is known that the two films mostly have a quasi-2D perovskite structure. The emission maximum wavelength of the PEA-FA perovskite film was 527 nm, that of the NMA-FA perovskite film was 530 nm, the PL quantum yield of the PEA-FA perovskite film was 64%, and that of the NMA-FA perovskite film was 60%. Apart from these, the emission spectra of the films were measured at 30 K, and the full-width at half-maximum of the emission peak of the PEA-FA perovskite film was 9 nm and that of the NMA-FA perovskite film was 8 nm. Thus, a sharp emission peak was observed in these. This indicates that each perovskite film has few crystal defects and has a high crystallinity.

In the transient decay curves of emission at 30 K shown in FIG. 5, no difference is seen between the PEA-FA perovskite film and the NMA-FA perovskite film, and the emission lifetime of the films was 120 ns. On the other hand, regarding the transient decay curves of emission at 300 K, the NMA-FA perovskite film has a decay pattern not differing from that at 30 K, while the PEA-FA perovskite film is seen to have a short lifetime component having an emission lifetime of 155 ns and a long lifetime component having an emission lifetime of 853 nm. In FIG. 7, no change is seen in the transient decay curve of emission of the NMA-FA perovskite film even when the temperature was elevated from 100 K up to 300 K. As opposed to this, as in FIG. 6, the long lifetime component tends to gradually increase in the PEA-FA perovskite film with increase in the temperature from 100 K up to 300 K. Here, the behavior of the excited triplet energy formed in the inorganic component is analyzed based on the transient decay curves of emission, and first, it is considered that the short lifetime emission observed in the NMA-FA perovskite film may be an emission based on the excited singlet energy level $E_S$ of the inorganic component. However, since the excited triplet energy level $E_{T1}$ of the organic component (NMA) is lower than the excited triplet energy level $E_T$ of the inorganic component, energy transfer occurs from the excited triplet energy level $E_T$ of the inorganic component to the excited triplet energy level $E_{T1}$ of the organic component (NMA), and therefore delayed fluorescence of a long lifetime component cannot be observed. Also in the PEA-FA perovskite film, it is considered that the short lifetime emission may be an emission based on the excited singlet energy level $E_S$ of the inorganic component. Since the excited triplet energy level $E_{T1}$ of the organic component (PEA) is higher than the excited triplet energy level $E_T$ of the inorganic component, energy transfer from $E_T$ to $E_{T1}$ does not occur. Namely, the observed emission of the long lifetime component is presumed to be a thermal activation type delayed fluorescence owing to radiation deactivation in transfer of the excited singlet energy to the excited singlet energy level of the organic-inorganic perovskite through reverse intersystem crossing from the excited triplet state to the excited singlet state. This process is a thermal activation process, and therefore the proportion of the long lifetime component increases with the increase in the sample temperature. Specifically, from the transient decay curves of emission in FIGS. 5 and 6, it is known that, when the difference between the excited singlet energy level $E_S$ and the excited triplet energy level $E_T$ in emission of the inorganic component is reduced to make the excited triplet energy level $E_{T1}$ of the organic component (PEA) higher than the excited triplet energy level $E_T$ of the inorganic component, then reverse intersystem crossing from the excited triplet state to the excited singlet state comes to be easier in the inorganic component and the excited triplet energy can be used as delayed fluorescence.

(Example 2) Production of Electroluminescent Device Using PEA-FA Perovskite Film A glass substrate having, as formed thereon, an anode of indium tin oxide (ITO) having a thickness of 100 nm (sheet resistance 12 Ω/sq) was prepared. On the ITO film, PVK was dropwise applied, spin-coated at 1000 rpm for 45 seconds, and baked at 120° C. for 30 minutes to form a PVK film having a thickness of 40 nm.

Next, in the same manner as in Example 1, a PEA-FA perovskite precursor solution having a concentration of 0.4 M was prepared, and using this, a PEA-FA perovskite film having a thickness of 150 nm was formed.

Subsequently, on the PEA-FA perovskite film, thin films were layered at a vacuum degree of $10^{-4}$ Pa according to a vacuum evaporation method. First, on the PEA-FA perovskite film, TPBi was formed in a thickness of 40 nm. Next, lithium fluoride (LiF) was formed in a thickness of 0.8 nm, and then aluminum (Al) was vapor-deposited in a thickness of 100 nm to form a cathode, and further a glass substrate was put thereon and sealed up with a UV-curable resin to produce an electroluminescent device.

(Comparative Example 2) Production of Electroluminescent Device Using NMA-FA Perovskite Film In the same manner as in Example 1, a PVK film was formed on an ITO film formed on a glass substrate. In the same manner as in Comparative Example 1, an NMA-FE perovskite film having a thickness of 150 nm was formed on the PVK film. Subsequently, in the same manner as in Example 2, TPBi, lithium fluoride and aluminum were vapor-deposited in sequence on the NMA-FA perovskite film, and on the aluminum cathode, a glass substrate was put and sealed up with a UV-curable resin to produce an electroluminescent device.

FIG. 8 shows emission spectra of the electroluminescent devices produced in Example 2 and Comparative Example 2; FIG. 9 shows current density-voltage-luminance characteristics thereof and FIG. 10 shows current density-voltage-external quantum efficiency (EQE) characteristics thereof. Table 2 shows the emission characteristics of the electroluminescent devices. In FIGS. 9 and 10, "PEA-FA Perovskite Film" shows the electroluminescent device of Example 2 using a PEA-FA perovskite film; and "NMA-FA Perovskite Film" shows the electroluminescent device of Comparative Example 2 using an NMA-FA perovskite film.

device using a PEA-FA perovskite film, both the singlet excitons and the triplet excitons were converted into photons, but in the electroluminescent device using an NMA-FA perovskite film, only a part of the singlet excitons were converted into photons.

(Example 3) Production of Electroluminescent Device Using PEA-MA Perovskite Film A PEA-MA perovskite precursor solution was prepared in the same manner as in Example 1 except that an equimolar amount of methylammonium bromide ($CH_3NH_3Br$) was used in place of phenylethylammonium bromide ($C_6H_5CH_2CH_2NH_3Br$) in Example 1. Then in the same manner as in Example 2 except that the PEA-MA perovskite precursor solution was used in place of the PEA-FA perovskite precursor solution in Example 2, an electroluminescent device using a PEA-MA perovskite film was produced.

(Comparative Example 3) Production of Electroluminescent Device Using NMA-MA Perovskite Film An NMA-MA perovskite precursor solution was prepared in the same manner as in Comparative Example 1 except that an equimolar amount of methylammonium bromide ($CH_3NH_3Br$) was used in place of phenylethylammonium bromide ($C_6H_5CH_2CH_2NH_3Br$) in Comparative Example 1. Then in the same manner as in Comparative Example 2 except that the NMA-MA perovskite precursor solution was used in place of the NMA-FA perovskite precursor solution in Comparative Example 2, an electroluminescent device using an NMA-MA perovskite film was produced.

Each electroluminescent device produced in Example 3 and Comparative Example 3 was driven, and all the devices gave green color emission, and delayed fluorescence emission was confirmed in these. FIG. 11 shows current density-

TABLE 2

| | Perovskite Film | Maximum External Quantum Yield (%) | Maximum Luminance (at 6 V) (cd/m$^2$) | Current Efficiency (cd/A) | Emission Maximum Wavelength (nm) | Full-Width at Half-Maximum of Emission Peak (nm) | CIE Chromaticity Coordinate (x, y) |
|---|---|---|---|---|---|---|---|
| Example 2 | PEA-FA Perovskite Film | 12.4 | 5200 | 52.1 | 527 | 21 | (0.18, 0.76) |
| Comparative Example 2 | NMA-FA Perovskite Film | 3.4 | 500 | 16.3 | 531 | 21 | (0.20, 0.75) |

Each electroluminescent device was driven, and all the devices gave green color emission. As in Table 2, the electroluminescent device using a PEA-FA perovskite film of Example 2 had an external quantum yield nearly 4 times higher than that of the electroluminescent device using an NMA-FA perovskite film of Comparative Example 2, and the former was excellent also in luminance and current efficiency. Regarding the exciton forming factor β presumed from the external quantum efficiency, the factor of the electroluminescent device of Example 2 was 97%, and that of the electroluminescent device of Comparative Example 2 was 27%. The data suggest that in the electroluminescent voltage-lamp efficiency, luminance, external quantum efficiency (EQE) characteristics of the electroluminescent device produced in Example 3; and FIG. 12 shows current density-voltage-lamp efficiency, luminance, external quantum efficiency (EQE) characteristics of the electroluminescent device produced in Comparative Example 3. Table 3 shows emission characteristics of the electroluminescence devices. The electroluminescent device using a PEA-MA perovskite film of Example 3 had an external quantum yield nearly 9 times higher than that of the electroluminescent device using an NMA-MA perovskite film of Comparative Example 3, and the former was excellent also in luminance and current efficiency.

TABLE 3

| | Perovskite Film | Maximum External Quantum Yield (%) | Maximum Luminance (at 6 V) (cd/m$^2$) | Current Efficiency (cd/A) | Emission Maximum Wavelength (nm) | Full-Width at Half-Maximum of Emission Peak (nm) | CIE Chromaticity Coordinate (x, y) |
|---|---|---|---|---|---|---|---|
| Example 3 | PEA-MA Perovskite Film | 4.88 | 1545 | 15.2 | 528 | 20 | (0.15, 0.77) |
| Comparative Example 3 | NMA-MA Perovskite Film | 0.55 | 8 | 1.96 | 522 | 21 | (0.13, 0.76) |

From the above, it is known that, using an organic-inorganic perovskite film in which the difference between the excited singlet energy level $E_S$ and the excited triplet energy level $E_T$ in emission of the inorganic component is small (not more than 0.1 eV) and in which the excited triplet energy level $E_{T1}$ of the organic component (PEA) is higher than the excited triplet energy level $E_T$ of the inorganic component, both the singlet excitons and the triplet excitons are utilized for light emission, and accordingly, an electroluminescent device having an extremely high emission efficiency can be realized.

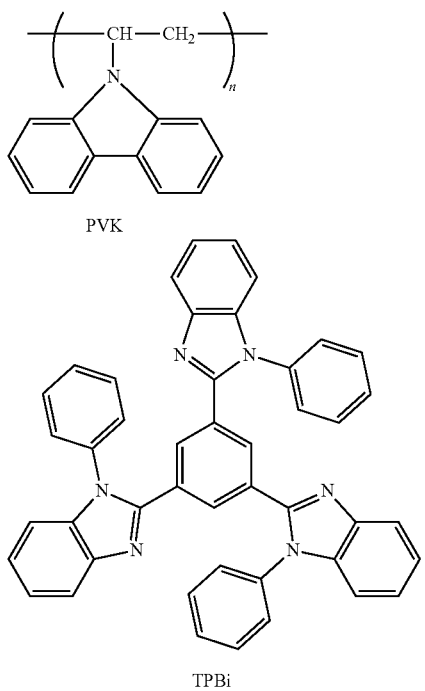

PVK

TPBi

INDUSTRIAL APPLICABILITY

The organic-inorganic perovskite of the present invention has a high emission efficiency and is inexpensive. Accordingly, using the organic-inorganic perovskite of the present invention as a light-emitting film of a light-emitting device, an inexpensive light-emitting device having a high emission efficiency can be provided. Consequently, the industrial applicability of the present invention is great.

REFERENCE SIGNS LIST

1 Substrate
2 Anode
3 Hole Injection Layer
4 Hole Transport Layer
5 Light-Emitting Layer
6 Electron Transport Layer
7 Cathode

The invention claimed is:

1. An electroluminescent device having an anode, a cathode, and a light-emitting layer between the anode and the cathode, wherein the light-emitting layer is composed of an organic-inorganic perovskite satisfying the following requirements (1) and (2) and represented by the formula (A) below:

$$E_T < E_{T1} \quad (1)$$

$$E_S - E_T \leq 0.1 \text{ eV} \quad (2)$$

wherein $E_S$ represents an excited singlet energy level in emission of an inorganic component constituting the organic-inorganic perovskite, $E_T$ represents an excited triplet energy level in emission of an inorganic component constituting the organic-inorganic perovskite, $E_{T1}$ represents an excited triplet energy level in emission of an organic component constituting the organic-inorganic perovskite $$PEA_2FA_{n-1}Pb_nBr_{3n+1} \quad (A)$$

wherein PEA represents a phenylethylammonim, FA represents a formamidinium, and n is 8.

2. The electroluminescent device according to claim 1, wherein the perovskite is a quasi-two-dimensional perovskite.

3. The electroluminescent device according to claim 1, which emits delayed fluorescence at 300 K.

* * * * *